(12) United States Patent
Oowaki et al.

(10) Patent No.: US 8,175,894 B2
(45) Date of Patent: May 8, 2012

(54) X-RAY EXPOSURE REPORT SYSTEM, MEDICAL APPARATUS, AND EXAMINATION PROTOCOL DISTRIBUTION SYSTEM

(75) Inventors: Naoki Oowaki, Otawara (JP); Yoichi Takada, Otawara (JP); Satoshi Ikeda, Yaita (JP); Fumiaki Teshima, Nasu-gun (JP); Akihiro Miyauchi, Kuroiso (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1915 days.

(21) Appl. No.: 11/071,347

(22) Filed: Mar. 4, 2005

(65) Prior Publication Data

US 2005/0209888 A1 Sep. 22, 2005

(30) Foreign Application Priority Data

Mar. 9, 2004 (JP) .................................. 2004-065685
Oct. 29, 2004 (JP) .................................. 2004-316747
Jan. 28, 2005 (JP) .................................. 2005-021902

(51) Int. Cl.
  *G06Q 10/00* (2012.01)
  *G06Q 50/00* (2012.01)
  *H05G 1/28* (2006.01)
(52) U.S. Cl. ................. 705/3; 705/2; 600/300; 378/165
(58) Field of Classification Search .................. None
See application file for complete search history.

(56) References Cited

U.S. PATENT DOCUMENTS 5,920,319 A * 7/1999 Vining et al. ................. 345/420
6,744,846 B2 * 6/2004 Popescu et al. ................. 378/16
6,751,600 B1 * 6/2004 Wolin ............................. 706/12
7,075,101 B2 * 7/2006 Iiyama .......................... 250/589
2001/0039503 A1 * 11/2001 Chan et al. ....................... 705/2
2002/0038392 A1 * 3/2002 De La Huerga ................. 710/8
2003/0095692 A1 * 5/2003 Mundy et al. ................. 382/128
2004/0078231 A1 * 4/2004 Wilkes et al. ..................... 705/2

FOREIGN PATENT DOCUMENTS

JP 4-317665 11/1992
(Continued)

OTHER PUBLICATIONS

Goto, Sachiko et al. "Measurement of Patient Exposure Dose on X-Ray Screening Mammography". IEEE Instrumentation and Measurement, Technology Conference, Budapest, Hungary, May 21-23, 2001.*

(Continued)

*Primary Examiner* — Luke Gilligan
*Assistant Examiner* — Anita Molina
(74) *Attorney, Agent, or Firm* — Oblon, Spivak, McClelland, Maier & Neustadt, L.L.P.

(57) ABSTRACT

A radiation report system includes a storage unit for storing a plurality of records including an exposure dose, an examination protocol, an examination part, a patient's age and a patient's weight with regard to the plurality of radiation examinations using a plurality of radiation diagnosis apparatuses. The plurality of records stored in the storage unit is classified into a plurality of groups based on the examination protocol, the examination part or patient information. An exposure report is created for each group based on the plurality of records stored in the storage unit. The data of the exposure report is served with a client side terminal.

17 Claims, 37 Drawing Sheets

FOREIGN PATENT DOCUMENTS

| | | |
|---|---|---|
| JP | 6-142089 | 5/1994 |
| JP | 10-155778 | 6/1998 |
| JP | 2002-163633 | 6/2002 |
| JP | 2002-277993 | 9/2002 |
| JP | 2002-288344 | 10/2002 |
| JP | 2003-79611 | 3/2003 |
| JP | 2003-175119 | 6/2003 |
| JP | 2003-271748 | 9/2003 |
| JP | 2003-310592 | 11/2003 |
| JP | 2004-105643 | 4/2004 |
| JP | 2004-201757 | 7/2004 |
| WO | WO 9837517 A1 * | 8/1998 |

OTHER PUBLICATIONS

Office Action issued in Aug. 24, 2010, in Japanese Patent Application No. 2005-021902 (with English-language translation).

* cited by examiner

| ACCESSION NO. | TOMOGRAPHY DATE | TOMOGRAPHY PART | AGE | CTDIw | DLP | WEIGHTS | CTDIw | DLP |
|---|---|---|---|---|---|---|---|---|
| 225113 | 2004/01/20 09:32:38 | CHEST | 52 YEARS | 98.4% | 90.6% | 68.3kg | 94.2% | 95.7% |
| 225116 | 2004/01/20 10:02:03 | ABDOMEN | 73 YEARS | 103.8% | 105.2% | 43.7kg | 192.1% | 173.9% |
| 225125 | 2004/01/20 10:25:41 | HEAD | 23 YEARS | 206.1% | 239.5% | 45.2kg | 103.1% | 105.2% |
| 225129 | 2004/01/20 11:10:10 | CHEST | 27 YEARS | 88.5% | 89.8% | 46.1kg | 85.6% | 87.9% |
| 225204 | 2004/01/20 11:45:54 | ABDOMEN | 19 YEARS | 104.1% | 106.5% | 44.6kg | 107.2% | 103.6% |

FIG. 9A

| ACCESSION NO. | TOMOG- RAPHY DATE | TOMOG- RAPHY TIME | AGE | | WEIGHT | | TOMOG- RAPHY PART | AGE | WEIGHT |
|---|---|---|---|---|---|---|---|---|---|
| | | | CTDIw | DLP | CTDIw | DLP | | | |
| 225113 | 2004/01/25 | 09:32:38 | 98.4% | 90.6% | 94.2% | 95.7% | CHEST | 52 YEARS | 68.3kg |
| 225116 | 2004/01/25 | 10:02:03 | 103.8% | 105.2% | 192.1% | 173.9% | ABDOMEN | 73 YEARS | 43.7kg |
| 225125 | 2004/01/25 | 10:25:41 | 206.1% | 239.5% | 103.1% | 105.2% | HEAD | 23 YEARS | 45.2kg |
| 225129 | 2004/01/25 | 11:10:10 | 88.5% | 89.8% | 85.6% | 87.9% | CHEST | 27 YEARS | 46.1kg |

| ACCESSION NO. | TOMOG- RAPHY DATE | TOMOG- RAPHY TIME | EP NO. | EXAMINATION PLAN NAME | TOMOG- RAPHY PART | AGE | WEIGHT |
|---|---|---|---|---|---|---|---|
| 225113 | 2004/01/25 | 09:32:38 | 59 | HCT C/A 20/5/5 CON | CHEST | 52 YEARS | 68.3kg |
| 225116 | 2004/01/25 | 10:02:03 | 34 | HCT CSP/MPR 1/15/2/2 | ABDOMEN | 73 YEARS | 43.7kg |
| 225125 | 2004/01/25 | 10:25:41 | 40 | HCT ABD 1/20/4/5 SR | ABDOMEN | 23 YEARS | 45.2kg |
| 225129 | 2004/01/25 | 11:10:10 | 40 | HCT ABD 1/20/4/5 SR | CHEST | 27 YEARS | 46.1kg |

FIG. 9C

| ACCESSION NO. | KVP | X-RAY TUBE CURRENT | TOTAL SCAN TIME (SEC) | CTDIw | DLP | AGE | TOMOG- RAPHY PART | EP NO. |
|---|---|---|---|---|---|---|---|---|
| 225113 | 120 | 240 | 49.36 | 23.7 | 2816.3 | 73 YEARS | CHEST | 59 |
| 225116 | 120 | 128 | 45.17 | 8.32 | 1143.9 | 100 YEARS | CHEST | 59 |
| AVERAGE | 120 | 184 | 47.265 | 16.01 | 1980.35 | 86.5 YEARS | | 59 |

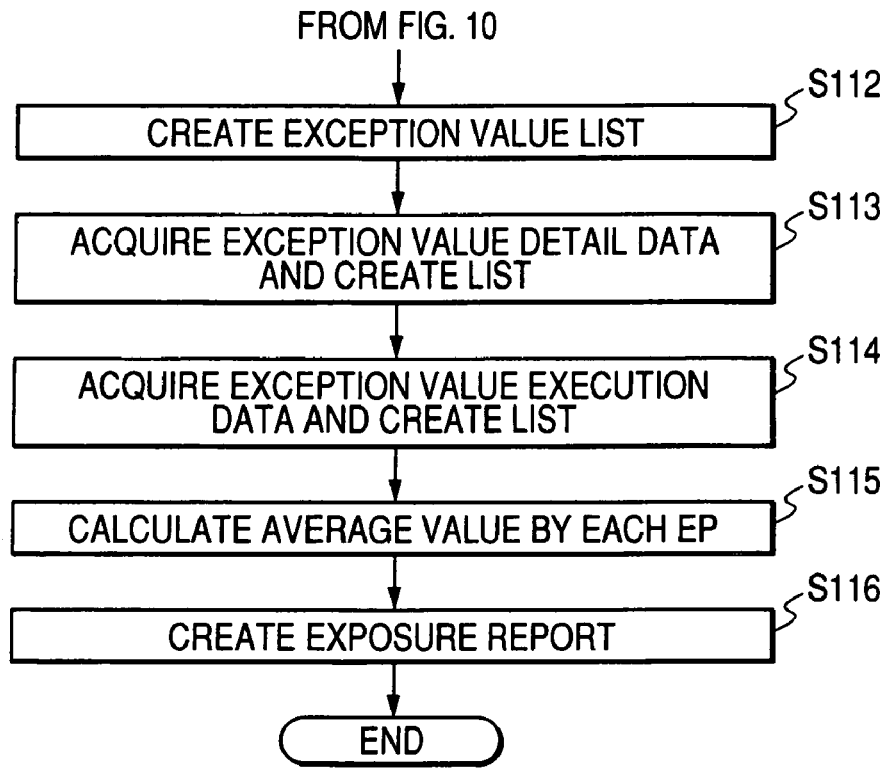
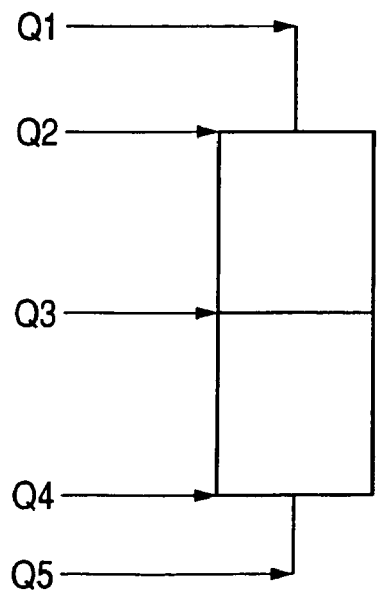

COMPARISON OBJECT FACILITY SELECTION STANDARD
SELECTING: SECTION

○ RECOMMENDED FACILITY
○ THE OTHER APPARATUS IN SELF-FACILITY
● FACILITY REFERENCE SELECTION

NEXT

FIG. 19

SELECTION OF THE OTHER APPARATUS IN SELF-FACILITY

○ A EXAMINATION ROOM
○ B EXAMINATION ROOM
● C EXAMINATION ROOM (REGISTRATION)    (STOP)

FIG. 20

COMPARISON OBJECT FACILITY SELECTION REFERENCE SELECTING

| <APPARATUS TYPE> | <APPARATUS MODEL> | <FACILITY TYPE> | <FACILITY SIZE> |
|---|---|---|---|
| ○ A APPARATUS | ○ A MODEL | ○ CEREBRAL NERVE | ○ 100 BEDS OR LESS |
| ○ B APPARATUS | ○ B MODEL | ○ CIRCULATORY ORGAN | ○ 100 TO 300 BEDS |
| ● C APPARATUS | ○ C MODEL | ○ RESPIRATORY ORGAN | ○ 300 TO 500 BEDS |
|  | ○ D MODEL | ○ DIGESTIVE ORGAN | ○ 500 BEDS OR MORE |
|  | ○ E MODEL | ○ NERVE |  |

(REGISTRATION)    (STOP)

FIG. 41

| Hospital Name: | | | | | | |
|---|---|---|---|---|---|---|
| Modality | CT | | | Report No. | 5829246 | |
| Model | #AQ16 | | | Report Date | 05/17/2004 2:17PM | |
| System ID | 211623 | | | Reporting Term | From: 05/09/2004 TO: 05/15/2004 | |

Dose Exception Report

| Accession # | Date Time | Body Region | Age | Age CTDIw | Weight (kg) | Weight CTDIw | Protocol solutions |
|---|---|---|---|---|---|---|---|
| 3524491 | 05/14/2004 21:09.32 | HEAD | 4Y | 275.6% | ... | 0% | Solution A |
| 3521814 | 05/12/2004 00:05.42 | CHEST | 36Y | 168.7% | 190.512000 | 164.7% | Solution B |
| 3521869 | 05/12/2004 04:19.52 | ABDOMEN | 72Y | 21.6% | 70.308000 | 21.6% | Solution C |
| 3521820 | 05/12/2004 03:45.06 | ABDOMEN | 80Y | 21.6% | 58.968000 | 21.6% | Solution C |
| 3521979 | 05/14/2004 14:16.42 | ABDOMEN | 50Y | 21.6% | 98.884800 | 21.6% | Solution C |
| 3521055 | 05/11/2004 14:43.34 | ABDOMEN | 54Y | 21.6% | 72.576000 | 21.6% | Solution C |

336

→ SCROLL

FIG. 42

SCROLL →

| Accession # | Date Time | EP # | EP Name (EXAMINATION OBJECT) | Category | Age | Weight |
|---|---|---|---|---|---|---|
| 3524491 | 05/14/2004 21:09:32 | 0 | ... | HEAD | 4Y | ... |
| 3521814 | 05/12/2004 00:05:42 | 38 | | CHEST | 38Y | 190.51200 |
| 3521869 | 05/12/2004 04:19:52 | 40 | | ABDOMEN | 72Y | 70.308000 |
| 3521820 | 05/12/2004 03:45:06 | 40 | | ABDOMEN | 80Y | 58.968000 |
| 3521979 | 05/14/2004 14:16:42 | 40 | | ABDOMEN | 50Y | 98.884800 |
| 3521055 | 05/11/2004 14:43:34 | 40 | | ABDOMEN | 54Y | 72.576000 |

| Accession # | Body Region | EP # | Weight | CTDIw | KVP | X-ray tube Current | Age | Total Rotation | Total Scan Time | Total mAs in Study |
|---|---|---|---|---|---|---|---|---|---|---|
| 3524491 | HEAD | 0 | ... | 60.1 | 120.0 | 250.0 | 4Y | 13 | 17.43 | 3479 |
| Average | | | (56.7) | (59.08) | (120) | (250) | (57.55) | (13.29) | (16.74) | (3578.13) |
| 3521814 | CHEST | 38 | 190.51200 | 26.8 | 120.0 | 325.0 | 38Y | 20 | 21.59 | 7107 |
| Average | | | (81.65) | (11.13) | (120) | (171.96) | (47.21) | (29.64) | (22.03) | (4943.57) |
| 3521869 | ABDOME | 40 | 70.308000 | 16.6 | 120.0 | 240.0 | 72Y | 33 | 26.49 | 7367 |
| Average | | | (81.65) | (14.92) | (120) | (216.36) | (65.27) | (31.09) | (24.25) | (6108.82) |
| 3521820 | ABDOME | 40 | 58.968000 | 16.6 | 120.0 | 240.0 | 80Y | 29 | 24.40 | 6464 |
| Average | | | (113.4) | (14.92) | (120) | (216.36) | (65.27) | (31.09) | (24.25) | (6108.82) |
| 3521979 | ABDOME | 40 | 98.884800 | 16.6 | 120.0 | 240.0 | 50Y | 23 | 20.27 | 5255 |
| Average | | | (65.77) | (14.92) | (120) | (216.36) | (65.27) | (31.09) | (24.25) | (6108.82) |
| 3521055 | ABDOME | 40 | 72.576000 | 16.6 | 120.0 | 240.0 | 54Y | 35 | 20.30 | 7701 |
| Average | | | (51.26) | (14.92) | (120) | (216.36) | (65.27) | (31.09) | (24.25) | (6108.82) |

FIG. 44

| HEAD | | | |
|---|---|---|---|
| 1.Solution A | Protocol Desciption | Solution A | Your Site |
| Scanner Information | Scanner<br>Scan Region<br>Scan Length<br>Scan Direction<br>Tube Voltage<br>Tube Current<br>Rotation time<br>Slice collimation<br>CT pitch factor<br>Total Scan Time<br>Scan Field<br># of Series | Acquilion 16<br>Head<br>178mm<br>Caudocranial<br>120kv<br>300mA<br>0.5s<br>16×0.5mm<br>0.6875:1(11:16)<br>16s<br>240mm<br>2 | Acquilion 16<br>Head<br>178mm<br>Caudocranial<br>120kv<br>250mA<br>0.3s<br>16×0.5mm<br>0.6875:1(11:16)<br>16s<br>240mm<br>2 |
| Reconstruction Information | Reconstruction Algorithm<br>Reconstruction Filter<br>Image Width<br>Reconstruction interval<br>Total number of images<br>Window width/Window lebel | TCOT<br>FC12,FC4<br>0.5mm,2mm<br>0.3mm,2mm<br>90,594<br>Multiple | TCOT<br>FC12,FC4<br>1.0mm,4mm<br>0.3mm,2mm<br>90,594<br>Multiple |
| Dose Information | Effective mAs<br>CTDIvol<br>DLP<br>Effective Dose<br>BERT | 218mAs<br>58.4mGy<br>1040mGy.cm<br>3.6mSv<br>18months | 218mAs<br>70mGy<br>1340mGy.cm<br>5.4mSv<br>18months |
| Contrast Information | Contrast<br>Concentration<br>Volume<br>Flow rate<br>Scan start method | Omniparue<br>300mgI/mL<br>100mL<br>4mL/s<br>SureStart | Omniparue<br>300mgI/mL<br>100mL<br>4mL/s<br>SureStart |

Image Sample 1

Image Sample 2

Image Sample 3

Image Sample 4

Protocol Simulator — 332

X-RAY EXPOSURE REPORT SYSTEM, MEDICAL APPARATUS, AND EXAMINATION PROTOCOL DISTRIBUTION SYSTEM

CROSS-REFERENCE TO RELATED APPLICATIONS

This application is based upon and claims the benefit of priority from prior Japanese Patent Applications No. 2004-065685, filed Mar. 9, 2004; No. 2004-316747, filed Oct. 29, 2004; and No. 2005-021902, filed Jan. 28, 2005, the entire contents of all of which are incorporated herein by reference.

BACKGROUND OF THE INVENTION

1. Field of the Invention

The present invention relates to an X-ray exposure report system for creating a report about an X-ray exposure such as an X-ray diagnosis, a medical apparatus, and an examination protocol distribution system for distributing an examination protocol to a client.

2. Description of the Related Art

A method using an X ray to diagnose or treat a patient is a useful method up to now. However, it is not possible to avoid being exposed to the X ray according to the diagnosis. Therefore, to know the exposure dose of the X ray with respect to the patient is an important problem in X-ray diagnosis therapy and it is also a matter of concern and interest to a user (doctor, examination engineer or the like).

An X-ray management apparatus that estimates and manages the X-ray exposure dose on the basis of an examination plan data has been known (for example, see Japanese Patent Laid-open No. 4-295172).

On the other hand, there is a service in that examination information of a medical diagnosis apparatus such as an X-ray CT apparatus is distributed to a user as a report. In such a service, information to support the improvement of examination efficiency based on the examination information or information about the quality maintenance of the diagnosis apparatus is transmitted to the user.

A hospital for performing an X-ray diagnosis therapy must manage an X-ray exposure dose to perform a safe examination, check whether an exception value such as an X-ray exposure dose having an extraordinary large value is generated or not, and change the setting of a parameter such that an examination can be performed with a small X ray. In addition, if the exception value is generated, it is necessary that in order to prevent the exception value from regenerating, the hospital seek to find a cause of the generation of the exception value and improve the parameter.

However, since the service and the system to support the management of the X-ray exposure dose have not generally be established, it is very difficult for the user to manage the X-ray exposure dose.

As is generally known, the environment surrounding the hospital management gradually becomes severe. In particular, in a department of radiation for introducing an image diagnosis apparatus and supplying image information and diagnosis report information, it is a very important problem awaiting solution in the management to analyze apparatus performance information such as the state of operation and the state of utilization in the image diagnosis apparatus to improve the efficiency of the management in the department of radiation to effectively use the image diagnosis apparatus.

In addition, it is required to provide the environment which can sufficiently induce the performance of an expensive image diagnosis apparatus and use the image diagnosis apparatus in the safe and reliable state. Particularly, it goes without saying that the protocol used in the apparatus is an important element in obtaining a clinical image.

However, since the image diagnosis apparatus is used for various diseases or diagnosis fields such as a circulatory organ, a digestive organ, a cerebral surgery or the like, the required image type or the required number of images is very different. In addition, it is necessary that the images be supplied according to the clinical request. Specifically, it is required that the examination protocol be supplied according to the task or problem of each user.

On the other hand, as disclosed in Japanese Patent Laid-open No. 2003-271748, there is a suggestion that in order to manage the exposure dose, a hospital side discovers the protocol or examination having an extraordinary large exposure dose to use it in improving the work.

Since the radiation management report, the apparatus utilization situation report, the protocol downloading, the exposure dose and the image quality simulation system are separated from each other, the protocol selection or the exposure dose/the image quality simulation cannot be made so as to correspond to the apparatus utilization situation of the user or the problem of the radiation management. As a result, it is difficult for the user to use it and the user must input the protocol information many times. In addition, it is not possible to provide a solving means (protocol download selection) with respect to the problems through the user sites.

BRIEF SUMMARY OF THE INVENTION

Accordingly, the present invention has been made to solve the above-mentioned problems, and it is an object of the present invention to support the management of an X-ray exposure dose of a user.

In order to achieve the above-mentioned object, according to a first aspect of the present invention, there is provided a radiation report system comprising: a storage unit for storing a plurality of records including an expose dose, an examination protocol, an examination part, a patient's age and a patient's weight with regard to a radiation examination using at least one radiation diagnosis apparatus; a grouping unit for classifying the plurality of records stored in the storage unit into a plurality of groups based on at least one of the examination protocol, the examination part, and the patient information; a report creating unit for creating an expose report for each group based on the plurality of records stored in the storage unit; and a server unit for serving data of the exposure report to a client side terminal.

According to a second aspect of the present invention, there is provided a radiation diagnosis apparatus comprising: an examination unit for carrying out a radiation examination with respect to a body to be examined; a storage unit for storing a plurality of records including an exposure dose, an examination protocol, an examination part, a patient's age and a patient's weight with regard to the radiation examination; a grouping unit for classifying the plurality of records stored in the storage unit into a plurality of groups based on at least one of the examination protocol, the examination part, and the patient information; a report creating unit for creating an exposure report for each group based on the plurality of records stored in the storage unit; and a display unit for displaying the exposure report.

According to a third aspect of the present invention, there is provided an examination protocol distribution system comprising: a storage unit for storing a plurality of records including an exposure dose, an examination protocol, and an examination object with regard to a plurality of radiation examinations carried out by a plurality of radiation diagnosis apparatuses arranged in a plurality of hospitals; an exception examination detecting unit for detecting records of which the exposure dose has an exception value from the plurality of records stored in the storage unit; a searching unit for searching from the storage unit the data of a plurality of examination protocols in another hospital of which the examination object is the same as the records of which the exposure dose has the exception value; and a server unit for serving data of the records of which the exposure dose has the exception value and the searched data of the examination protocol of another hospital to a client side terminal.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIGS. 9A to 9C are diagrams illustrating each display example of the actual exposure dose data in the first embodiment;

FIG. 11 is an explanatory view illustrating the operation subsequent to FIG. 10;

FIG. 12 is an explanatory view illustrating the location of a box plot in the first embodiment;

FIG. 19 is a diagram illustrating an input screen example for selecting the other apparatus when the other apparatus in a self-facility is selected in the input screen shown in FIG. 18;

FIG. 20 is a diagram illustrating an input screen example for selecting a facility when the facility reference is selected in the input screen shown in FIG. 18;

FIG. 41 is a diagram illustrating another example of tabulation in the exposure dose report of FIG. 37;

FIG. 42 is a diagram illustrating a next page of FIG. 41; and

FIG. 44 is a diagram illustrating detailed information of an examination protocol distributed by clicking a [Solution A] button in an abnormal exposure dose report of FIG. 43;

DETAILED DESCRIPTION OF THE INVENTION

First Embodiment

Figure 1:
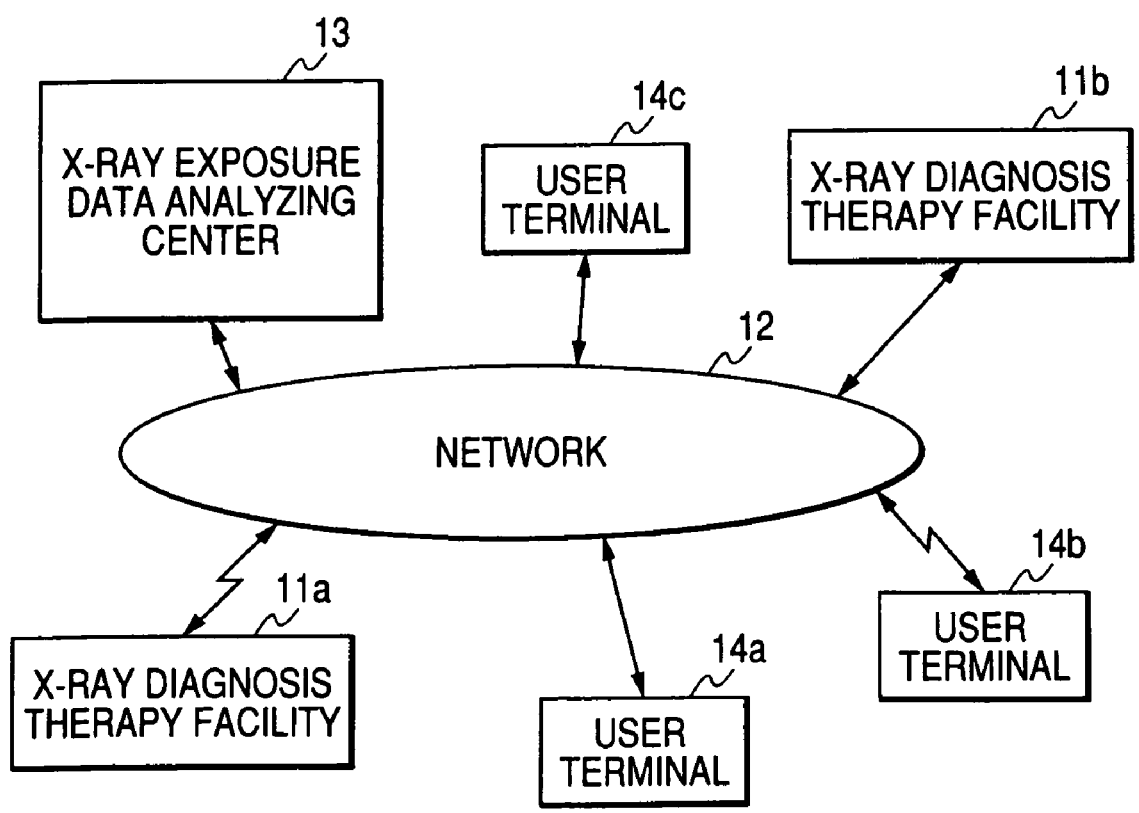
FIG. 1 is a diagram illustrating the structure of an overall system according to a first embodiment of the present invention.

Hereinafter, a first embodiment of the present invention will be described with reference to the accompanying drawings. FIG. 1 shows the structure of an X-ray exposure report system according to the first embodiment of the present invention that is constructed through a network. In FIG. 1, through a network 12, the X-ray exposure report system is connected to X-ray diagnosis therapy facilities 11a and 11b such as a hospital where an X-ray diagnosis apparatus and an X-ray therapy apparatus, which are described in detail later, are installed therein. The X-ray exposure report system comprises an X-ray exposure data ANALYZING CENTER 13 for analyzing X-ray exposure dose, creating a report and transmitting the report and user terminals 14a, 14b and 14c which are connected to the network 12 and on which the X-ray exposure dose can be displayed.

In this example, the number of the X-ray diagnosis therapy facilities is two and the number of the user terminals is three. However, the number of the X-ray diagnosis therapy facilities may be two or more or two or less and the number of the user terminals may be three or more or three or less.

Figure 2:
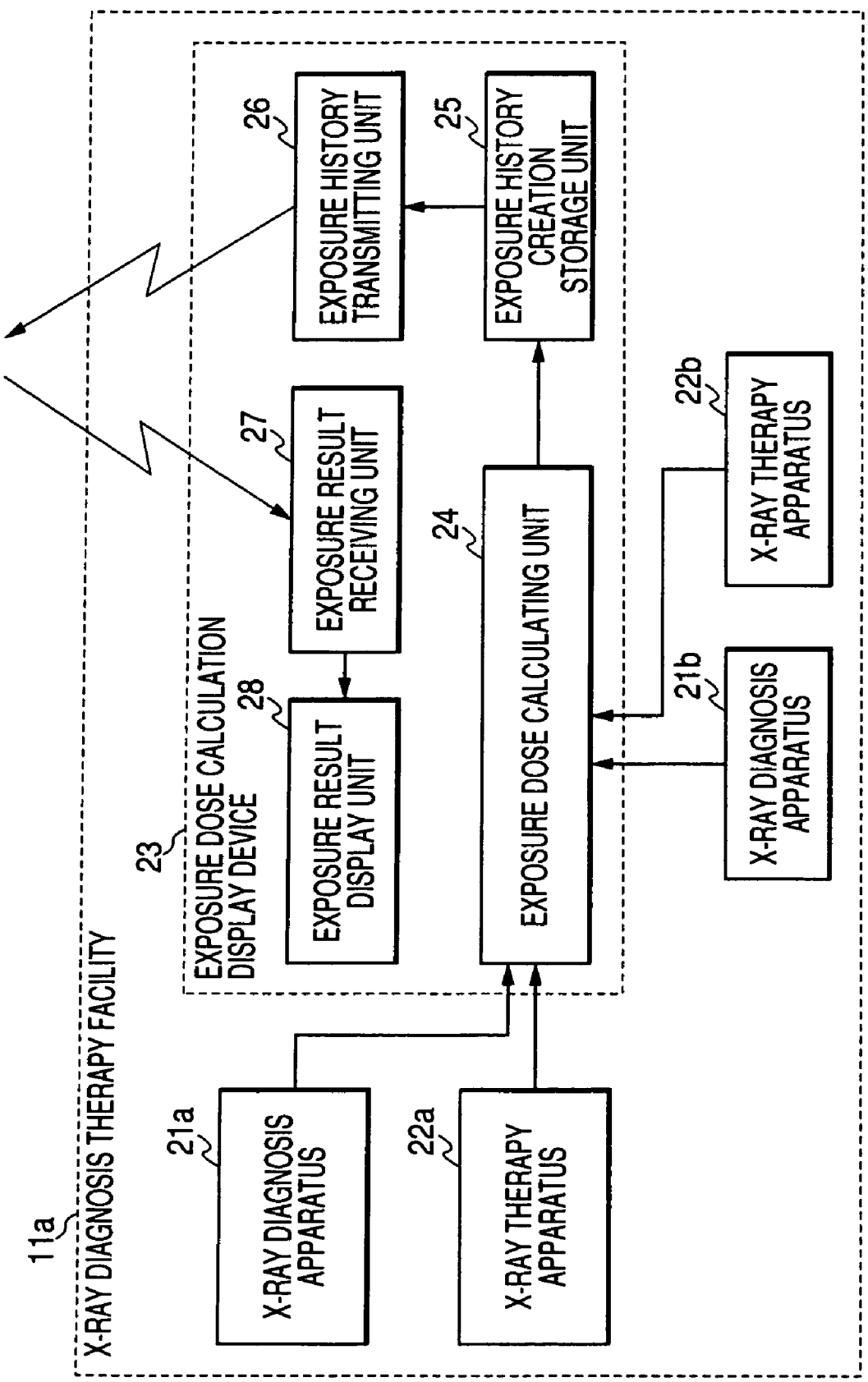
FIG. 2 is a diagram illustrating the structure of an X-ray diagnosis therapy facility in the overall system according to the first embodiment shown in FIG. 1.

As shown in FIG. 2, the X-ray diagnosis therapy facility 11a includes X-ray diagnosis apparatuses 21a and 21b or X-ray therapy apparatuses 22a and 22b and an exposure dose calculation display device 23 for calculating the X-ray exposure dose from the X-ray diagnosis therapy apparatus from an examination plan to display it.

The exposure dose calculation display device 23 includes an exposure dose calculation unit 24 for calculating a exposure dose (X-ray exposure dose) irradiated to a patient at the time of diagnosing and treating the patient in the X-ray diagnosis apparatuses 21a and 21b or the X-ray therapy apparatuses 22a and 22b based on an examination plan of each examination, an exposure history creation storage unit 25 for creating an exposure history calculated in the exposure dose calculation unit 24 to store it, an exposure history transmitting unit 26 for transmitting the exposure history created in the exposure history creation storage unit 25 to the below described X-ray exposure dose analyzing center 13 through the network, an exposure result receiving unit 27 for receiving the exposure result transmitted from the X-ray exposure dose analyzing center 13, and an exposure result display unit 28 for displaying the exposure result received from the exposure result receiving unit 27.

In addition, the X-ray exposure dose analyzing center 13 includes an exposure information receiving module 31, an exposure history database system (DB) 32 for storing the exposure history, an exposure report creation module 33 for comparing a predetermined reference exposure dose with an actual exposure dose stored in the exposure history database system (DB) 32 to determine it to create an exposure report, a task scheduler 34 for instructing the exposure report creation module 33 to create the report, and a mail server 35 and a Web server 40 for transmitting the exposure report through the mail and the web.

The exposure information receiving module 31 includes an exposure history receiving unit 36 for receiving the exposure history from the exposure dose calculation display device 23 of the X-ray diagnosis therapy facility 11a and an exposure result registration unit 37 for registering the result of the exposure history received by the exposure history receiving unit 36 in the exposure history DB 32.

The exposure report creation module 33 includes an exposure reference setting unit 38 for setting a threshold value serving as a reference value in order to determine whether the exposure dose is a normal value and an exception value, a reference exposure data storage unit 39 for storing the reference exposure dose set by the exposure reference setting unit 38, an exposure data comparison unit 41 for comparing the reference exposure dose stored in the reference exposure data storage unit 39 with the actual exposure dose stored in the exposure history DB 32, an exposure result determination storage unit 42 for determining whether the actual exposure dose is greater than the reference exposure dose based on the result of the comparison by the exposure data comparison unit 41, and an exposure report creation unit 43 for creating an exposure report when it is determined by the exposure result determination storage unit 42 that the actual exposure dose is greater than the reference exposure dose.

In addition, an exception examination means an examination of which the exposure dose is exceptionally high among a plurality of past actual examinations which becomes report objects and the exception value means the exposure dose of the exception examination. A value for discriminating whether the exposure dose is exceptionally high or not is called a reference value or a threshold value.

Here, the reference exposure dose (threshold value) is compared with the actual exposure dose calculated on the basis of the examination plan. It is determined that the actual exposure dose higher than the reference exposure dose is in the exception value which is out of the standardized range of the exposure dose. A specific meaning of the exception value is determined according to various setting methods of the reference exposure dose, which will be described in detail later.

The report created by the exposure report creation unit 43 is transmitted to a user through the mail server 35. However, the report is uploaded onto the Web server 40 such that the user can see the report.

Figure 4:
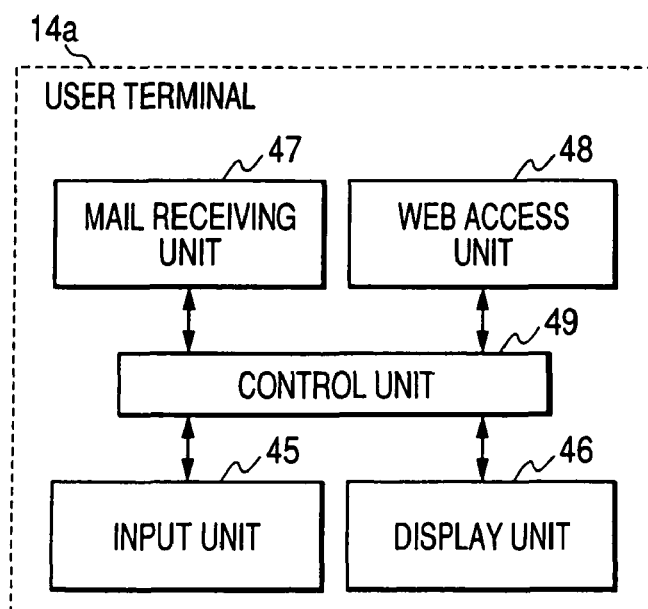
FIG. 4 is a diagram illustrating the structure of a patient terminal shown in FIG. 1.

As shown in FIG. 4, the user terminal 14a includes an input unit 45 through which the user can input data, a display unit 46 for displaying exposure data or graph to the user, a mail receiving unit 47 for receiving the mail transmitted from the mail server 35 of the X-ray exposure data ANALYZING CENTER 13, a Web access unit 48 which can see the exposure report uploaded onto the Web server 35 of the X-ray exposure data ANALYZING CENTER 13, and a control unit 49 for controlling the entire user terminal.

Next, the operation of the present embodiment will be described with reference to a flowchart shown in FIG. 5. When a radiation is irradiated to a specific patient from the X-ray diagnosis apparatuses 21a and 21b and the X-ray therapy apparatuses 22a and 22b of the X-ray diagnosis therapy facility 11a shown in FIG. 2, the X-ray exposure dose is calculated in the exposure dose calculation unit 24 based on the examination plan at that time. Since a time is recorded on the data of the actual exposure dose, it is apprehended when the exposure through the X-ray is performed. The calculation results are sequentially input in the exposure history creation storage unit 25, the data of the actual exposure dose is created for each patient, and the created data is stored therein (step S501).

The data of the actual exposure dose temporarily stored in the exposure history creation storage unit 25 is transmitted from the exposure history transmitting unit 26 to the X-ray exposure data ANALYZING CENTER 13 through the network 12 every predetermined time using a protocol such as FTP. The data of the X-ray exposure dose transmitted to the X-ray exposure data ANALYZING CENTER 13 is received in the exposure history receiving unit 36 to be input in the exposure result registration unit 37 (step S502). Next, in step S503, the X-ray exposure data is transmitted from the exposure result registration unit 37 to the exposure history DB 32 and is registered therein (step 503). The exposure history registration by this time is regularly performed for every examination based on the examination plan having been carried out.

The task scheduler 34 controls the operation of the exposure report creation module 33 and instructs the exposure report creation module 33 to create the exposure report whenever the exposure report is requested.

In addition, the exposure reference setting unit 38 in the exposure report creation module 33 is constructed such that the exposure reference setting unit 38 can set the reference exposure dose data to compare it with the actual exposure dose data, and the reference exposure dose data set in the exposure reference setting unit 38 is previously stored in the reference exposure data storage unit 39.

Figure 5:
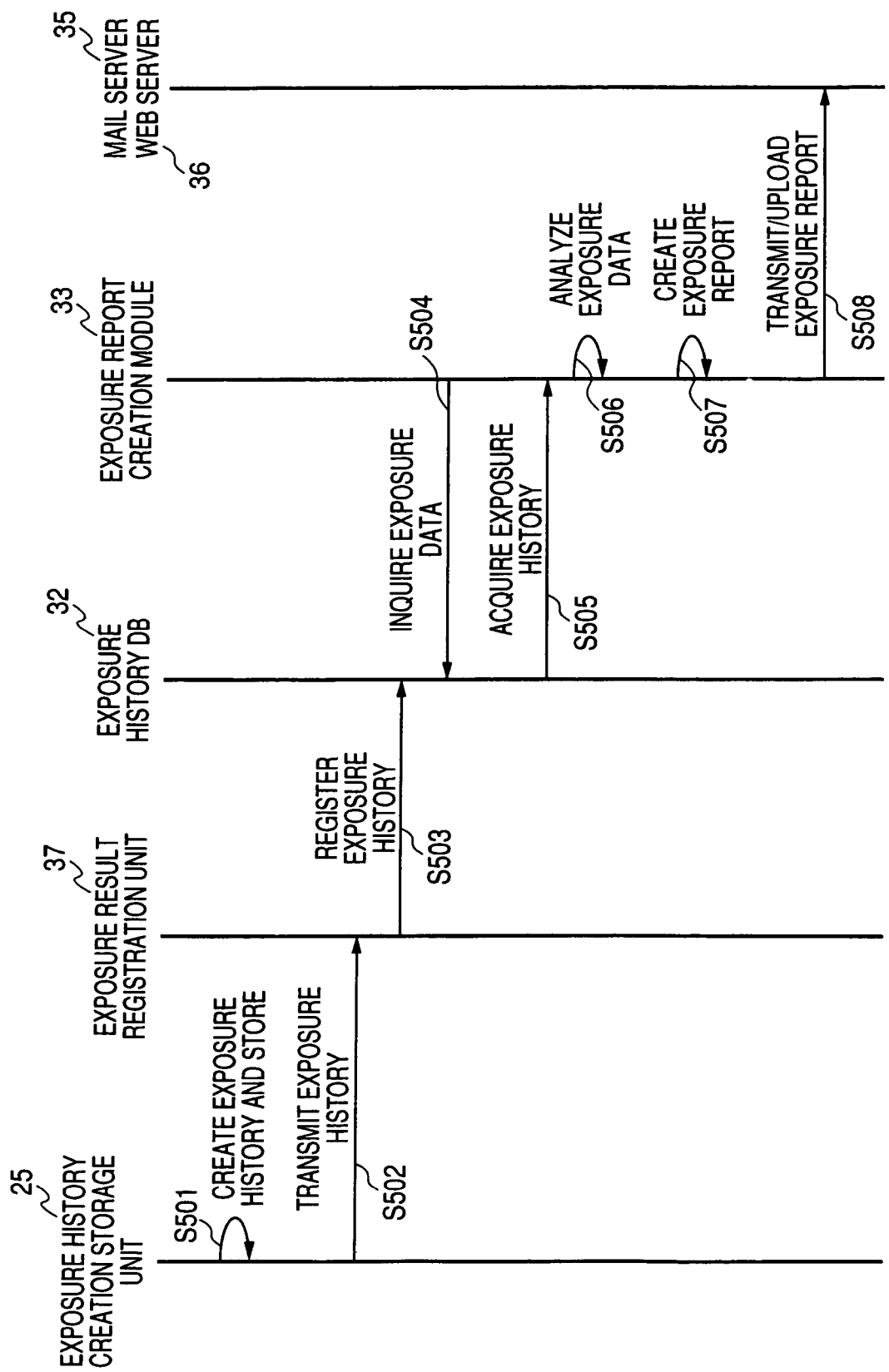
FIG. 5 is an explanatory view illustrating the operation of the first embodiment.

On the other hand, when the exposure report creation module 33 receives the instruction of the exposure report creation from the task scheduler 34, in step S504 shown in FIG. 5, the exposure data comparison unit 41 makes reference to the exposure history DB 32 about the exposure history.

When the exposure data comparison unit 41 acquires the exposure history of the actual exposure dose from the exposure history DB 32 (step S505), the exposure data comparison unit 41 compares the acquired actual exposure dose data with the specific reference exposure dose data stored in the reference exposure data storage unit 39 to transmit the comparison result into the exposure result determination storage unit 42. The exposure result determination storage unit 42 determines whether the actual exposure dose data is abnormal or not to transmit the determined result into the exposure report creation unit 43.

In this way, the analysis of the actual exposure dose data in the step S506, that is, the comparison between the actual exposure dose and the reference exposure dose and the determination are performed by the exposure data comparison unit 41 and the exposure result determination storage unit 42.

The exposure report creation unit 43 creates the report according to the result input from the exposure result determination storage unit 42 (step S507). The report created in the exposure report creation unit 43 is transmitted to the user terminals or the X-ray diagnosis therapy facilities from the mail server 35 through the electronic mail and is uploaded by the Web server 40 (step S508).

In addition, for example, the report and display content through the mail server 35 and the Web server 40 may be different from each other such that the exposure report transmitted from the mail server 35 through the electronic mail represents the specific data and the general tendency is displayed on the Web server 40.

The exposure report transmitted through the electronic mail is received by the mail receiving unit 47 of the user terminal 14a, so that the user can see the exposure report through the display unit 46. In addition, the user has access to the Internet through the Web access unit 48 in the user terminal 14a, so that the user can see the exposure report uploaded from the Web server 40 through the display unit 46.

In addition, the exposure report is transmitted to the X-ray diagnosis therapy facility 11a and is received by the exposure result receiving unit 27 of the exposure dose calculation display device 23 to be displayed on the exposure result display unit 28.

On the other hand, the exposure information is calculated by the exposure dose calculation unit 24 of the X-ray diagnosis therapy facility 11a, the exposure history thereof is created by the exposure history creation unit 25, the exposure information is transmitted from the exposure history transmitting unit 26 to the X-ray exposure data ANALYZING CENTER 13 to be received by the exposure history receiving unit 36, and the exposure information is registered in the exposure history DB 32 from the exposure result registration unit 37. In the exposure information, with regard to the exposure when the CT scan is performed by the X-ray CT apparatus, an unique ID of apparatus, a slice width, KVP (X-ray tube voltage), an exposure time, an X-ray tube voltage, an examination part, rotation times, a TOMOGRAPHY time, mAs (index indicating a total X-ray tube current value of a scan time. Calculated by an X-ray tube current and an actual exposure time set by an examination plan), CTDIw (TOMOGRAPHY Dose Index Weighted; an exposure dose per a thickness of a unit slice), DLP (Dose Length Product; total exposure dose), an examination type, a patient's age, a weight, a height, examination date and time, an examination time, FOV (TOMOGRAPHY region), the number of sheets of TOMOGRAPHY images, an instruction doctor's name, and an examination engineer's name.

Figures 6, 7:
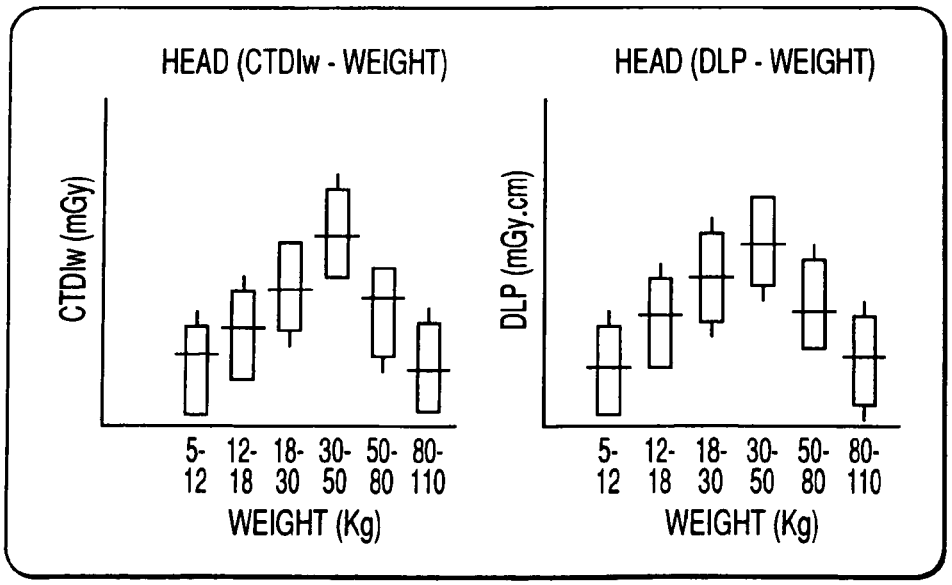
FIG. 6 is a diagram illustrating an example of the exposure data display in the first embodiment.
FIG. 7 is a diagram illustrating an example of the data display of the reference exposure dose in the first embodiment.

Next, a display format that the exposure report is displayed on the screen of the exposure result display unit 28 in the exposure dose calculation display device 23 will be described. FIG. 6 shows an example of the exposure report displayed on the screen of the exposure result display unit 28. The accession No indicates an accession number assigned to each examination plan of each patient, and TOMOGRAPHY data and time, a TOMOGRAPHY part, an age, CTDIw, DLP, a weight, a CTDIw, and a DLP are displayed for each accession No. Here, the values with respect to the standard CTDIw and the standard DLP at the corresponding age are displayed with a percentage on the CTDIw column and the DLP column next to the age column and the values with respect to the standard CTDIw and the standard DLP at the weight are displayed with a percentage on the CTDIw column and the DLP column next to the weight.

In FIG. 6, for example, the data of the TOMOGRAPHY image of a first row of accession No 225113 indicates information that a patient's chest is tomographed at 09:32 on Jan. 20, 2004, a patient is 52 years old, the CTDIw and DLP values of the patient are respectively 98.4% and 90.6% with respect to the standard values of 52 years, the weight of the patient is 68.3 Kg, and the CTDIw and DLP values of the patient are respectively 94.2% and 95.7% with respect to the standard values of the weight 68 Kg.

In FIG. 6, the data of the TOMOGRAPHY image of the third row of accession No 225125 indicates information that a patient's head is tomographed at 10:25 on Jan. 20, 2004, a patient is 23 years old, the CTDIw and DLP values of the patient with respect to the standard value of 23 years are 206.1% and 239.5%, respectively, the weight of the patient is 45.2 Kg, and the CTDIw and DLP values of the patient with respect to the standard value of the weight 45 Kg are 103.1% and 105.2%, respectively. By displaying this screen, there is an advantage in that the user can see only the exposure data of the exception value collectively.

Although not shown in FIG. 6, when the CTDIw and DLP values of the patient exceeds 200% with respect to the standard values, the corresponding cells are displayed with red colors, and when the CTDIw and DLP values of the patient exceeds 100% with respect to the standard values, the corresponding cells are displayed with yellow colors. Therefore, reference numerals 61 and 62 of FIG. 6 are displayed with the yellow colors and reference numerals 63 and 64 are displayed with the red colors on the screen. In this way, if displaying the cells with different colors, there is an advantage in that it is possible to precisely determine to what extent the exposure dose of a specific patient is higher than a common exposure dose.

In addition, when the locations of the CTDIw and DLP values are clicked, a range of a standard value of the exposure dose with respect to the age or weight can be displayed. For example, when a part corresponding to a reference numeral 65 of FIG. 6 is clicked, the screen is displayed as shown in FIG. 7.

A graph located at the left side of FIG. 7 shows a CTDIw value commonly exposed when a head of a person having a weight within a predetermined range is tomographed and a graph located at the right side of FIG. 7 shows a DLP value commonly exposed when a head of a person having a weight within a predetermined range is tomographed. In addition, a line dividing a box corresponding to each weight range into the upper and lower sides indicates the boundary between a high level 25% of the frequency and a low level 25% of the frequency.

Therefore, by clicking the cell corresponding to the reference numeral 65 of FIG. 6, it is possible to apprehend the location of the CTDIw value in the overall values whether the CTDIw value of the patient is 103.1%.

In addition, the data can be displayed on the upper half of the screen of the exposure result display unit 28 like FIG. 6 and the graph can be displayed on the lower half of it like FIG. 7. In the graphs shown in FIG. 7, an x axis indicates a weight range and a y axis indicates a CTDIw value and a DLP value. However, there is even a case where an age is indicated in an x axis. Moreover, the X-ray exposure dose such as the CTDIw, the DLP, mAs (X-ray tube current value x actual exposure time) or the like is displayed on the y axis. The X-ray exposure dose can be provided to each display title of a disease name, a disease code, an examination plan, an examination name code and DPC as well as for the examination part.

Figure 8:
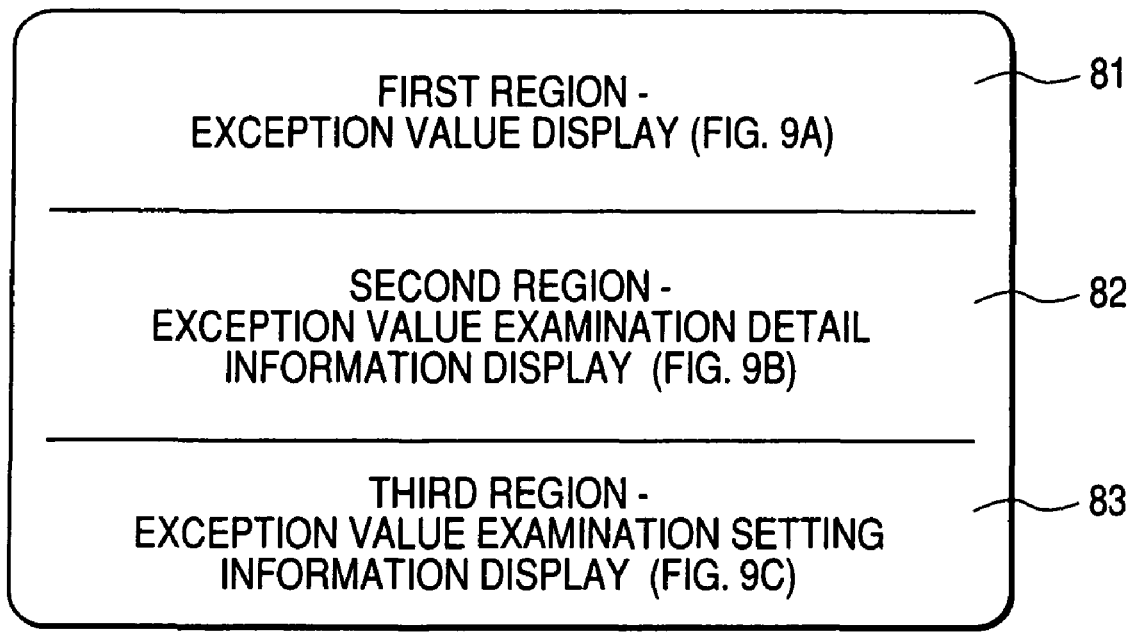
FIG. 8 is a diagram entirely illustrating a display example of the exception value data of the actual exposure dose in the first embodiment.

FIG. 8 shows another display format of the X-ray exposure dose of the patient. In this example, a screen is displayed so as to be divided into three parts of first to third regions, and an exception value is displayed on a first region 81 of an upper stage, detailed information of the exception value examination is displayed on a second region 82 of a middle stage and an exception value examination setting information is displayed on a third region 83 of a lower stage.

Specifically, as shown in FIG. 9A, on the first region 81, a TOMOGRAPHY date, a TOMOGRAPHY time, a relative value (%) of the corresponding patient with respect to the standard CTDIw and DLP values of a patient's age, a relative value (%) of the corresponding patient with respect to the standard CTDIw and DLP values of a patient's weight, a TOMOGRAPHY part, a patient's age and a patient's weight are displayed for every an accession number.

For example, a reference numeral 91 of FIG. 9A indicates that the DLP value of the corresponding patient is 90.6% with respect to the standard DLP value of a patient that is 52 years old. In this case, as shown in FIG. 7, the ranges of the standard CTDIw and DLP values of the TOMOGRAPHY part with respect to the age or weight can be displayed on the different screen or the lower half of one screen.

In addition, as shown in FIG. 9B, on the second region 82, each row of TOMOGRAPHY data displays a TOMOGRAPHY date, a TOMOGRAPHY time, an examination plan number (EP NO.) displayed as an exception value, an examination plan name, a TOMOGRAPHY part, a patient's age and a patient's weight are displayed for every accession number.

In addition, as shown in FIG. 9C, on the third region 83, setting values, that is, KVP, an X-ray tube current, a total scan time (a total time necessary for an examination), CTDIw, DLP, an age, a TOMOGRAPHY part, and EP No. are displayed every accession No. In addition, a scan length, a slice width or the like can be displayed. By comparing theses values with each other, it is possible to easily determine why the corresponding values of the patient are the exception values.

In addition, as shown in FIG. 9C, the average values of the detailed information in the respective embodiments of the comparison object data may be displayed.

Figure 10:
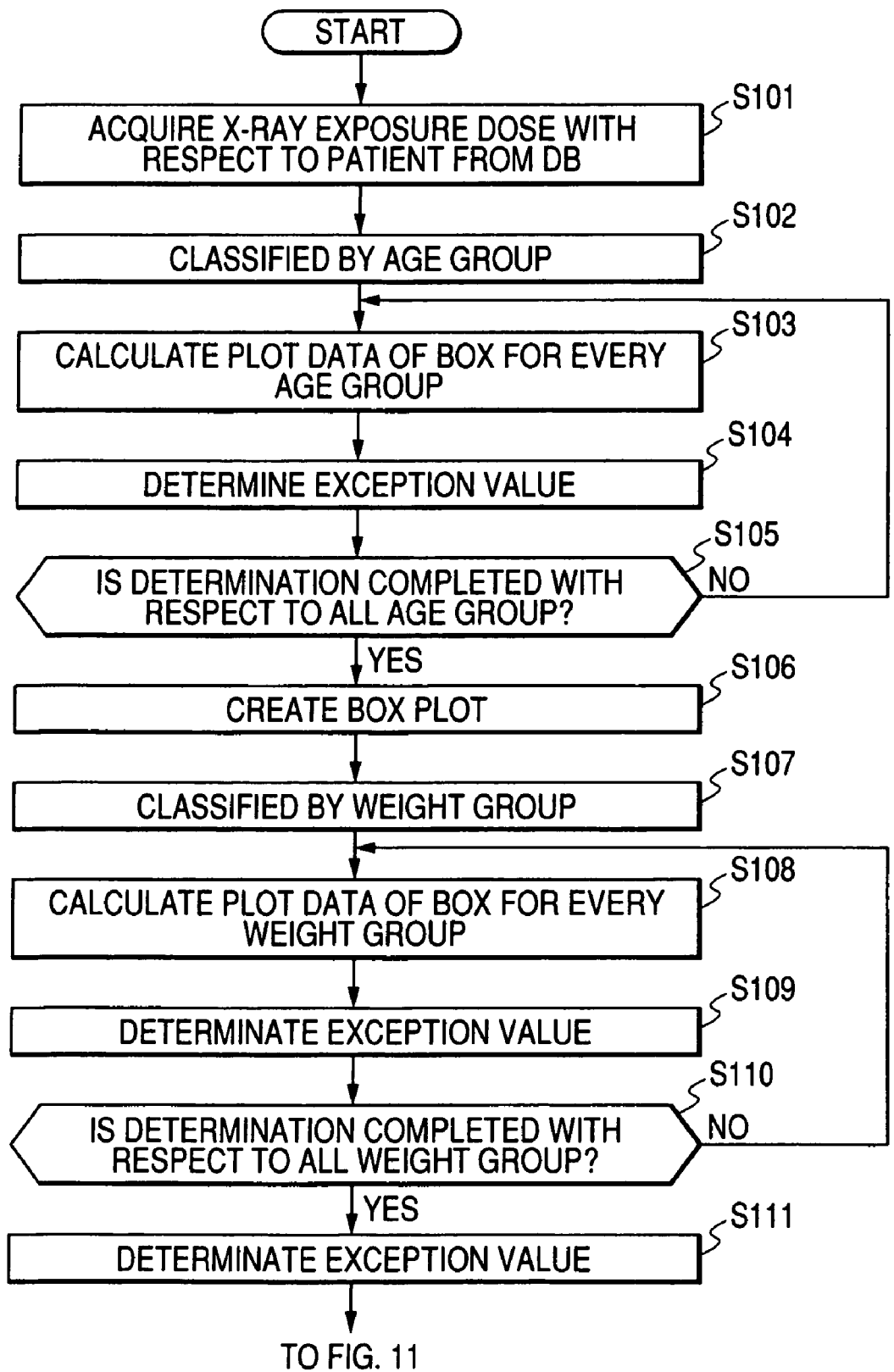
FIG. 10 is an explanatory view illustrating the operation for creating the exposure report in the first embodiment.

The exposure report created by the exposure report creation module 33 of the X-ray exposure data ANALYZING CENTER 13 shown in FIG. 3 will be described based on a flowchart illustrated in FIG. 10.

In the reference exposure data storage unit 39, an age, data of the standard CTDIw and DLP values for each weight or the like are stored in the reference exposure data storage unit 39 as described below. The exposure data comparison unit 41 acquires from the exposure history DB 32 the X-ray exposure dose irradiated to the patient by the corresponding apparatus corresponding to the report period using the identifier of the apparatus used for the TOMOGRAPHY as a key (step 101). The acquired X-ray exposure dose data includes an accession No, CTDIw, DLP, EP No. (examination plan number), a TOMOGRAPHY part, an age, and a weight.

In step 102, the acquired exposure data is classified by an age, box plot data of the CTDIw and DLP are calculated in each age group which is classified (step 103), and the result is firstly stored.

In next step S104, the exposure data comparison unit 41 compares the data with data supplied from the reference exposure data storage unit 39 so that the determination of the exception value data of the CTDIw and DLP in each age group is performed. When the corresponding data has the exception value, an accession No (corresponding to an order number) serving as the identifier of the corresponding examination is temporarily stored in the exposure result determination storage unit 42.

In step 105, it is checked whether the determination of the exception value is completed with respect to all age groups. If the determination is not completed, the process returns to the step S103, so that the determination of the exception value is performed with respect to the age groups of which the determination is not completed.

After it is confirmed that the determination of the exception value is completed with respect to the all age groups in the step S105, in step S106, a box plot is created using the firstly stored exposure data to be stored in the result determination storage unit 42 again.

In next step S107, the exposure data acquired from the exposure history DB 32 is classified by a weight group. In step S108, the box plot data for each weight group is calculated, and in step S109, the determination of the exception value data is performed in each weight group. When the corresponding data has the exception value, an accession No serving as the identifier of the corresponding examination is firstly stored in the exposure result determination storage unit 42. In step S110, it is checked whether the determination of the exception value is completed with respect to all weight groups. If the determination is not completed in some weight group, the process returns to the step S108, so that the box plot data is calculated with respect to the weight groups of which the determination is not completed and the determination of the exception value is performed in step S109.

After it is confirmed that the determination of the exception value is completed with respect to the all weight groups, in step S111, the determination of the exception value is performed again. After that, the process enters into the step S112 illustrated in FIG. 11 to create a list with respect to the firstly stored exception value.

In next step S113, the detailed information of the examination having the exception value is acquired from the exposure history DB 32 by the accession No which is previously temporarily stored and the a detailed list of the exception value data as shown in FIG. 9B is created. In this case, the acquired detailed information includes information such as examination date and time, a time when the examination is carried out, an EP number, CTDIw, DLP, and a TOMOGRAPHY part.

In next step S114, the information of examination performance having the exception value is acquired from the exposure history DB 32 using the previously stored accession No, the list of the exception value data is created and the average value is calculated for each EP in step S115.

Figure 3:
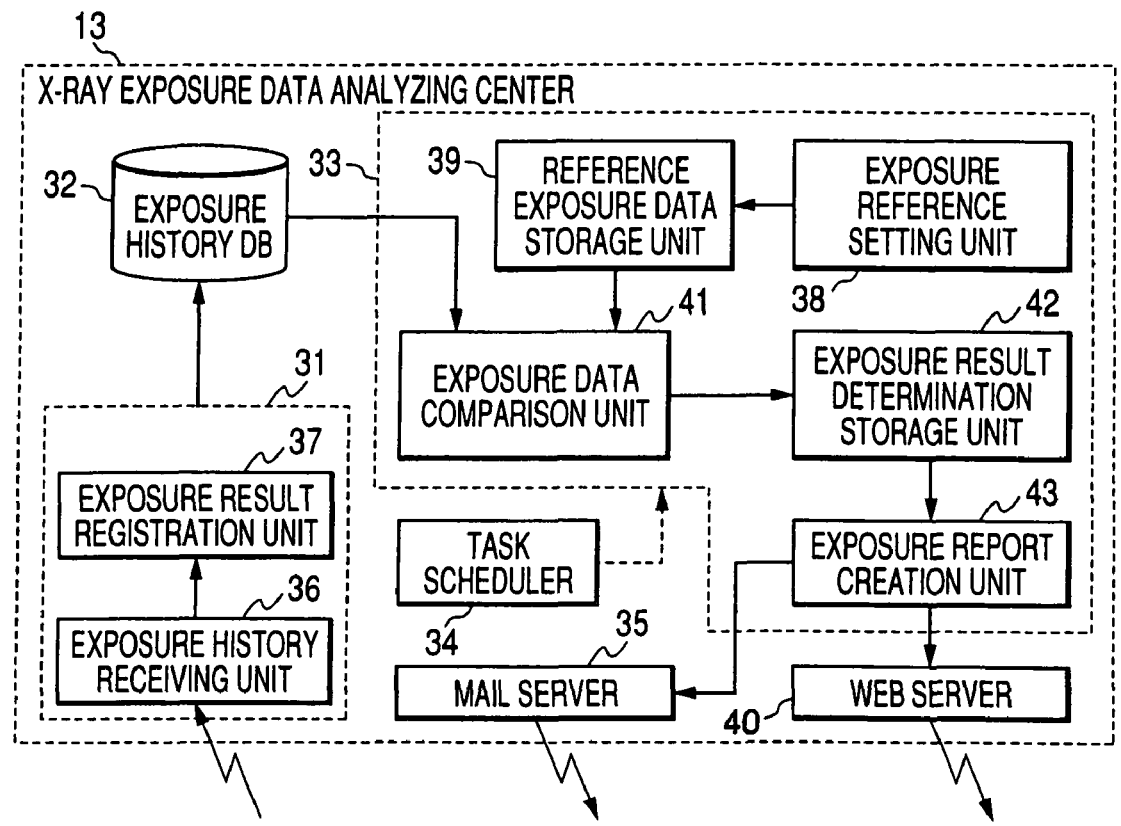
FIG. 3 is a diagram illustrating the structure of an X-ray exposure data ANALYZING CENTER shown in FIG. 1.

In step S116, the exposure report creation unit 43 shown in FIG. 3 collects the lists created in the above-mentioned manner to create the exposure report, and the exposure report is transmitted through the electronic mail from the mail server 35 and is transmitted to the Web server 40 to be uploaded.

Next, a display method of the box plot used in the present invention will be described.

As shown in FIG. 12, an upper side value of a box is Q1, the upper limit of the box is Q2, an average value of the box is Q3, the lower limit of the box is Q4, and a lower side value of the box is Q5. At this time, Q1 to Q5 are represented by the following formulas.

It is set that the total number of all data is N and D(n) indicates a value of the n-th data when all the data is sorted in descending order. When a value of Q2 is 87.5%, $$\text{Quarter } 1 = (int)(N+1) \times 0.125, \quad (1)$$

$$ADP(\text{after\_the\_decimal\_point}) = (N+1) \times 0.125 - \text{Quarter } 1, \quad (2)$$

$$Q2 = D(\text{Quarter } 1) + ADP \times \{D(\text{Quarter } 1 + 1) - D(\text{Quarter } 1)\}, \quad (3)$$

When a value of Q4 is 12.5%, $$\text{Quarter } 3 = (int)(N+1) \times (0.875), \quad (4)$$

$$ADP(\text{after\_the\_decimal\_point}) = (N+1) \times 0.875 - \text{Quarter } 3, \quad (5)$$

$$Q4 = D(\text{Quarter3}) + ADP \times \{D(\text{Quarter } 3 + 1) - D(\text{Quarter3})\}, \quad (3)$$

When a value of Q1 is 100%, Q1=a maximum value.
When a value of Q3 is 50% (mean), if N is an even number, $$Q3 = [D\{(N+1) \div 2\} + D\{(N+1) \div 2 + 1\}]2, \text{ (average value)} \quad (4)$$

When N is an odd number, $Q3 = D\{(N+1) \div 2\}$, (5)

When a value of Q5 is 0%, Q5=a minimum value.
A calculation method of a threshold value is as follows.
When a value of Q2 is 75%, $$\text{Quarter } 1 = (int) (N+1) \times 0.25, \quad (6)$$

ADP (after_the_decimal_point)

$$= (N+1) \times 0.25 - \text{Quarter } 1, \quad (7)$$

$$Q2 = D(\text{Quarter } 1) + ADP \times \{D(\text{Quarter } 1 + 1) - D(\text{Quarter } 1)\}, \quad (8)$$

When a value of Q4 is 25%, $$\text{Quarter } 3 = (int) (N+1) \times (0.75), \quad (9)$$

ADP (after_the_decimal_point)

$$= (N+1) \times 0.75 - \text{Quarter } 3, \quad (10)$$

$$Q4 = D(\text{Quarter } 3) + ADP \times \{D(\text{Quarter } 3 + 1) - D(\text{Quarter } 3)\}, \quad (11)$$

The threshold value of Q1 is represented by a following formula.

$$Q1 = Q2 + 1.5 \times (Q2 - Q4), \quad (12)$$

On the other hand, in the present invention, Q1 calculated by the method is used for calculating the exception value. If any data D(i) is greater than Q1, the data D(i) is defined as the exception value.

It may be determined whether any data is the exception data based on Q1 calculated by the method.

In the present invention, the exposure reference setting unit 38 of the X-ray exposure data ANALYZING CENTER 13 shown in FIG. 3 can have as the threshold value the setting value defined in the external organization and the user can define the threshold value. The embodiment corresponding to the description will be described in the latter part.

Figure 13:
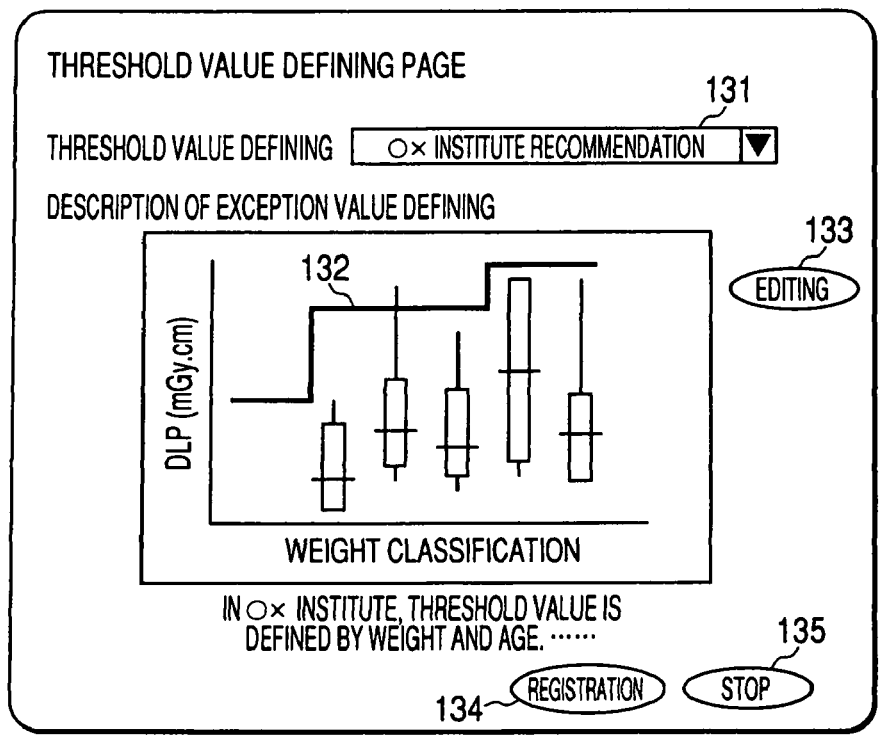
FIG. 13 is a diagram illustrating a display example when the characteristics of the exception value are acquired from the outside in the first embodiment.

FIG. 13 shows an example using a threshold value recommended by O×institute at the time of determining the exception value. When the O×institute recommendation is selected in a field 131 of a threshold value definition of FIG. 13, for example, a value of the DLP with respect to the weight classification is displayed at the lower side of the field 131 of the threshold value definition. The line indicated by a reference numeral 132 determines a threshold value with respect to each weight classification in this graph.

Figure 14:
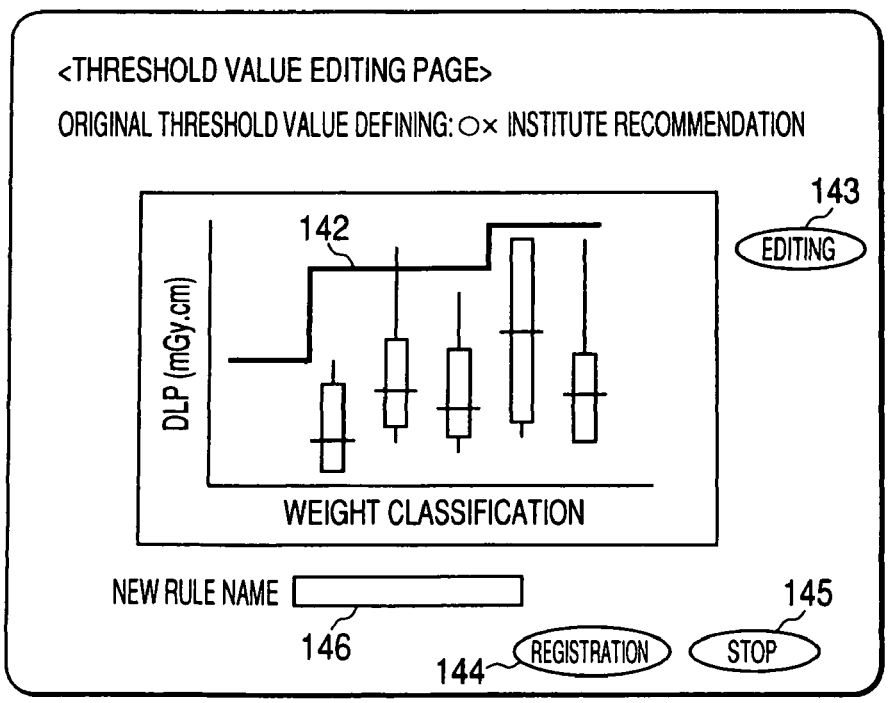
FIG. 14 is a diagram illustrating a display example when a user modifies the characteristics of the exception value after the characteristics of the exception value are acquired from the outside in the first embodiment.

An editing button 133, a registration button 134, and a stop button 135 are displayed near the graph. When adopting the threshold value recommended by the O×institute, the registration button 134 may be clicked. When the editing button 133 of FIG. 13 is clicked, for example, the screen shown in FIG. 14 is displayed, so that the user can change the setting of the threshold value 142. As described above, when the characteristic of the exception value is changed, by inputting a file name stored in a field 146 of a new rule name and clicking the registration button 144, the changed characteristic of the exception value can be stored. After that, the characteristic of the exception value can be called by the file name.

Figure 15:
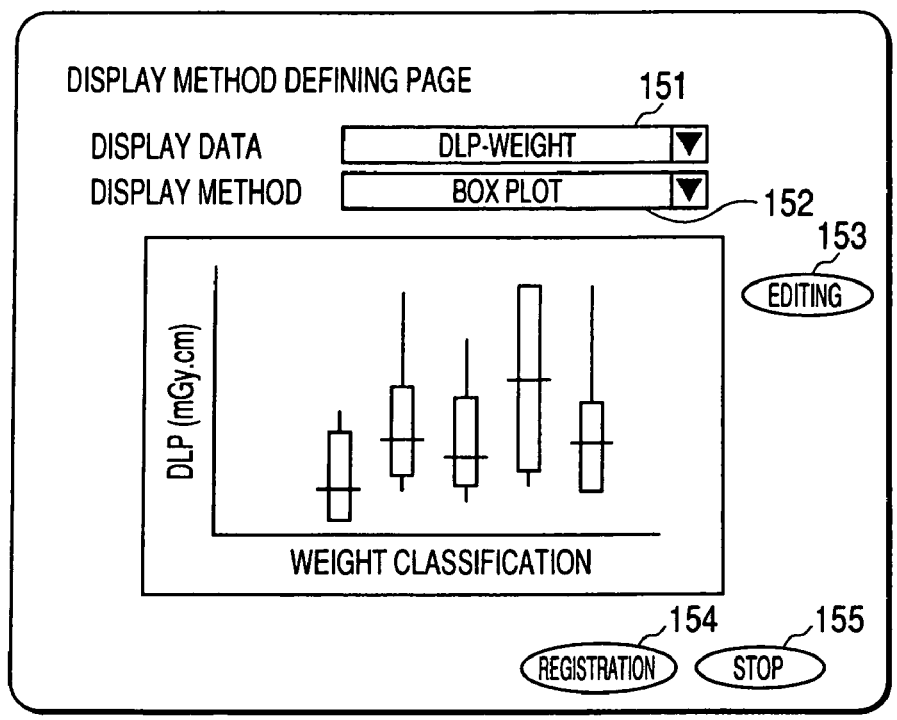
FIG. 15 is a diagram illustrating an input example when a user selects display data and a display method in the first embodiment.

In the present invention, the distribution of the X-ray exposure dose may be displayed by the box plot method and may be displayed by another display method such as a plotting. In other words, as shown in FIG. 15, only when a selection field 152 of the display method is selected by the box plot, the display using the box plot method is performed. In this case, in a selection field 151 of the display data, displaying the graph of the DLP and weight is selected. Specifically, in this example, the display data can be selected from a drop menu and the display method can be selected from a drop menu. A sample graph is displayed at the lower side of the drop menus. In this screen, when clicking the registration button 154, the selected content is transmitted to the X-ray exposure data ANALYZING CENTER 13 together with the user identification information to be stored therein.

Figure 16:
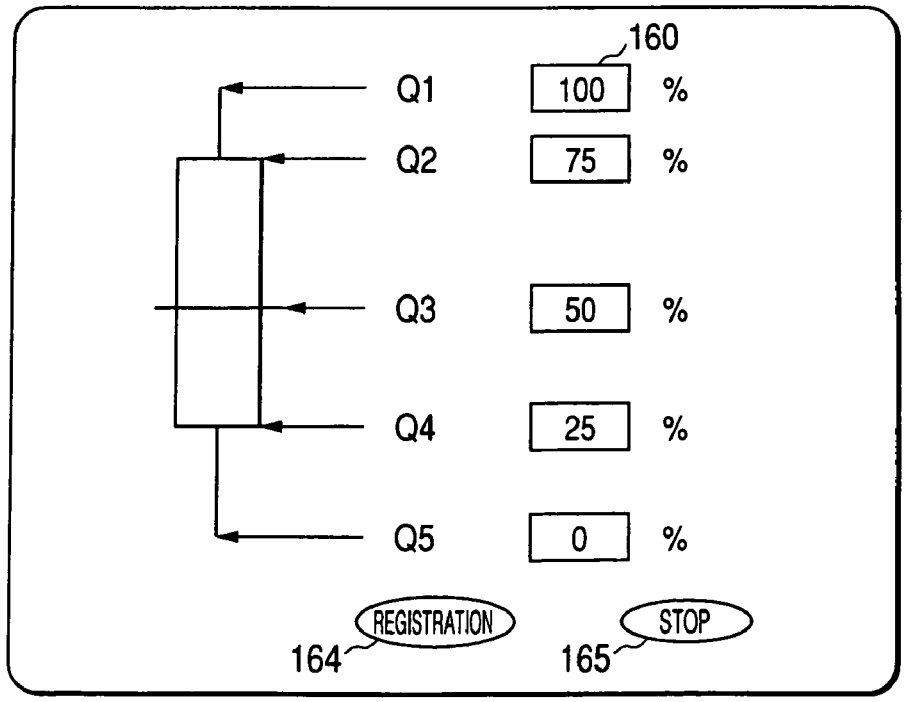
FIG. 16 is a diagram illustrating an input example when each location of the box display to be displayed is defined by a user in the first embodiment.

In addition, when clicking the editing button 153, as shown in FIG. 16, it is possible to define the details of the display method of the box plot. In FIG. 16, the data values from Q1 to Q5 can be input. After inputting these values, when clicking the registration button 164, the definition of the box plot is performed.

On the other hand, the threshold value of the X-ray exposure dose may be determined as the characteristic of the threshold value (benchmark) with respect to the weight or age as described above. The case in which the benchmark method is applied to the analysis of the exception value of the exposure dose will be described. The X-ray exposure data ANALYZING CENTER 13 shown in FIG. 3 acquires the previously determined comparison object data and the exposure data by the report object apparatus to compare them with each other. The comparison object data is examination data of a specific apparatus, a specific hospital or a specific hospital group.

In the X-ray exposure data ANALYZING CENTER 13, when the data of the X-ray exposure dose exceeds the threshold value of the data of the comparison object group, it is regarded as the exception value, so that the exposure data is displayed on the first region as shown in FIG. 8.

Next, a second example of the case to which the benchmark method of the X-ray exposure dose is applied will be described. Here, the case in which the distributions of the exposure dose are compared with each other will be described. The X-ray exposure data ANALYZING CENTER 13 acquires the previously determined comparison object exposure data and the report object exposure data. The comparison object exposure data is examination data of a specific apparatus, a specific hospital, or a specific hospital group. Here, the case in which the data of the specific hospital is used as the comparison object data will be described. The exposure data comparison unit 41 of the X-ray exposure data ANALYZING CENTER 13 obtains from the exposure history DB 32 the distribution of the actual exposure dose data of a report object and the distribution of the exposure data of a comparison object to display the comparison result.

Figures 17, 18:
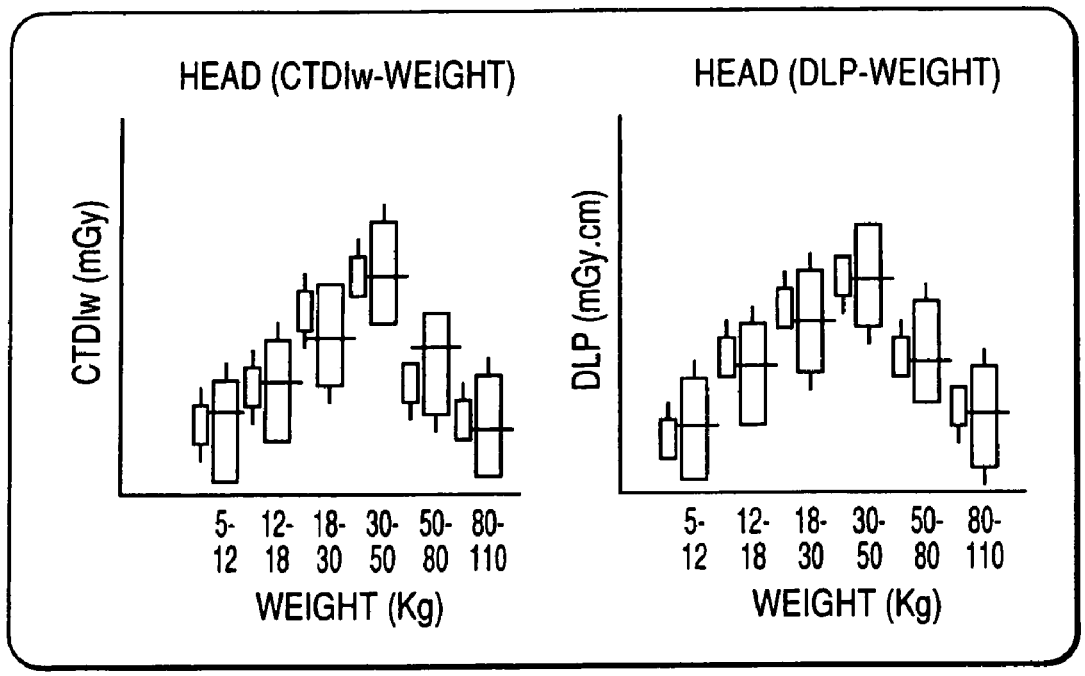
FIG. 17 is a diagram illustrating a display example when the reference exposure dose and the actual exposure dose are compared with each other through the box display in the first embodiment.
FIG. 18 is a diagram illustrating an input screen example when a selection reference of a comparison object facility is selected by a user in the first embodiment.

An example of this case is shown in FIG. 17. A box plot having a small size indicates comparison object exposure data and a box plot having a large size indicates report object data supplied from the exposure history DB 32. The comparison object exposure data and the report object data are displayed parallel to each other.

FIG. 17 shows the case in which the comparison between the CTDIw value and the weight and the comparison between the DLP value and the weight are performed in the range of the weight. However, the comparison may be performed for each of the age range, the examination name code DPC, the disease name, the examination part, and the examination plan.

In the present invention, the user can select the comparison object exposure data. For example, as shown in FIG. 18, as sections, a recommendation facility, the other apparatus in a self-facility and a facility reference selection are displayed in a format of a threefold choice. When the recommendation facility is selected, it is compared with the previously selected exposure data of the recommendation facility. In this case, the additional setting is not required.

When the other apparatus in the self-facility is selected, as shown in FIG. 19, if the other apparatuses in the self-facility, for example, an A examination room, a B examination room, and a C examination room are in the self-facility, these examination rooms are displayed on a next screen. By selecting one apparatus from the apparatuses, the comparison object data is specified.

On the other hand, on the screen shown in FIG. 18, when the facility reference selection is selected, as shown in FIG. 20, as facility reference, an apparatus type, an apparatus model, a facility type, and a facility size are displayed such that these items can be selected. BY selecting these items suitably, the facility of a comparison object is specified.

In a description of the embodiment of the present invention, performing the exposure report every predetermined time is described. However, it is not limited to performing the exposure report every predetermined time, but the exposure report can be performed whenever the report is required, that is, when the actual exposure dose exceeds the reference exposure dose.

In a description of the embodiment of the present invention, the X-ray exposure data ANALYZING CENTER and the exposure dose calculation display device in the X-ray diagnosis therapy facility are connected to each other through the a network. The network may be a local area network (LAN) in the medical facility such as the hospital, may be a wide area network (WAN) using a public line and may be an Internet.

In addition, the X-ray exposure data ANALYZING CENTER and the exposure dose calculation display device in the X-ray diagnosis therapy facility may be directly connected to each other, the exposure dose calculation display device may be included in each X-ray diagnosis therapy apparatus or the exposure dose calculation unit which is a part of the exposure dose calculation display device may be included in each X-ray diagnosis therapy apparatus.

The actual exposure dose in the present embodiment is calculated based on the examination plan of each examination. However, the actual exposure dose irradiated to the patient may be calculated or may be indirectly calculated from the actual exposure dose irradiated to the patient.

In addition, in the description of the above-mentioned embodiment, the case in which the exposure report is displayed on the exposure result display unit in the exposure dose calculation display device is described. However, the exposure report may be displayed on the terminal of the user.

The first embodiment has the following aspect.

Figure 21:
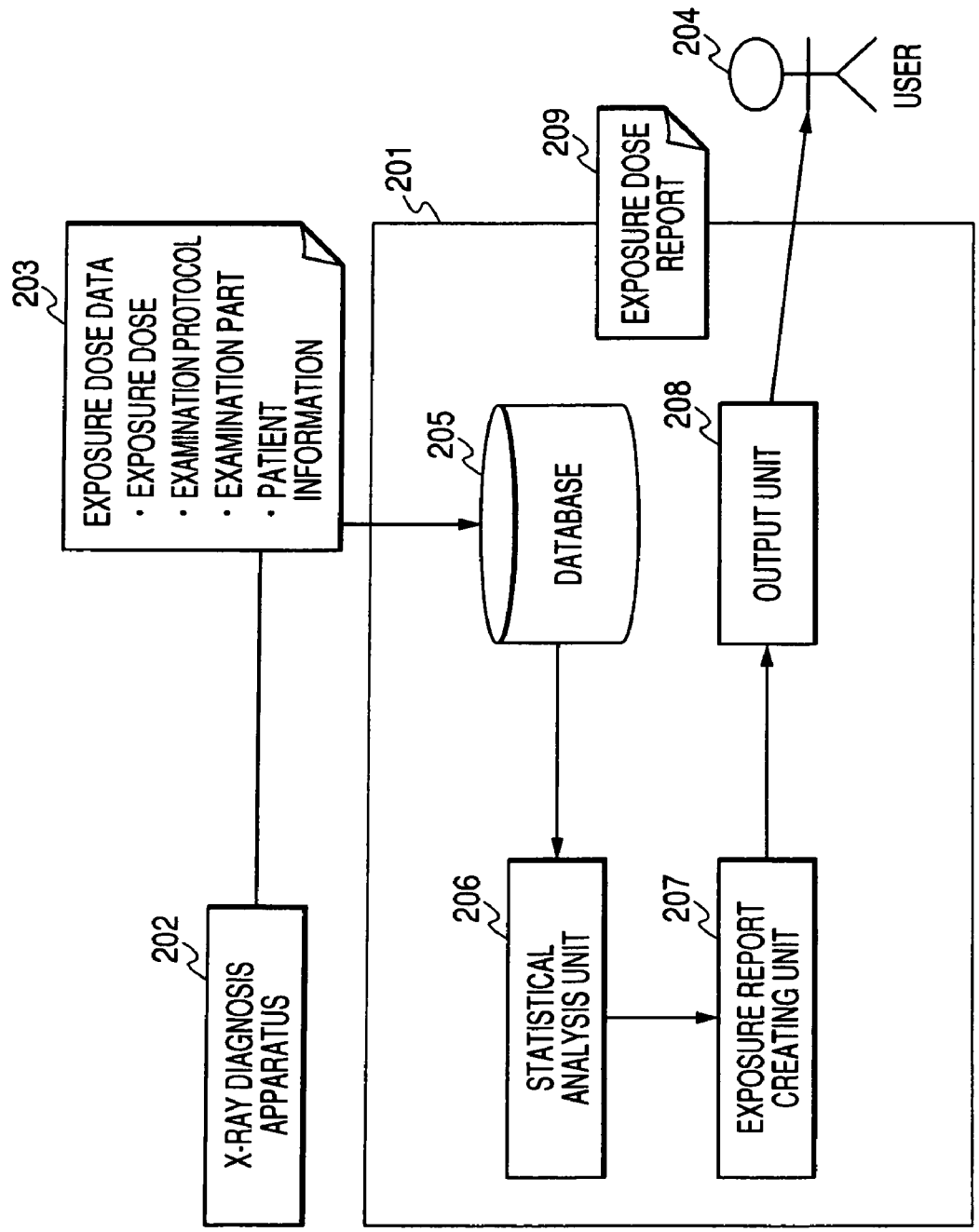
FIG. 21 is a diagram illustrating another structure of a data ANALYZING CENTER 13 according to the first embodiment.
Figure 22:
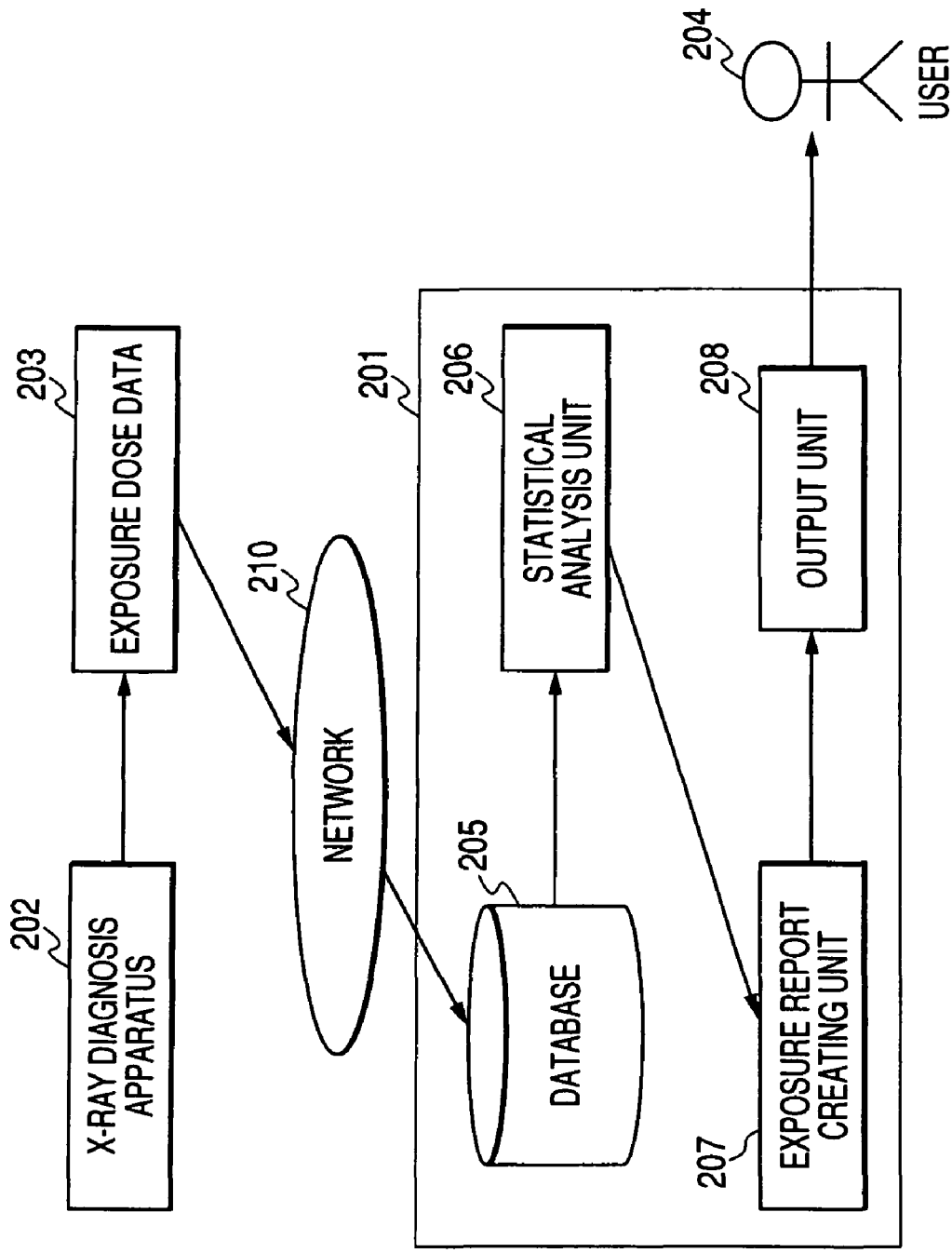
FIG. 22 is a diagram illustrating the structure of a network of FIG. 21.
Figure 23:
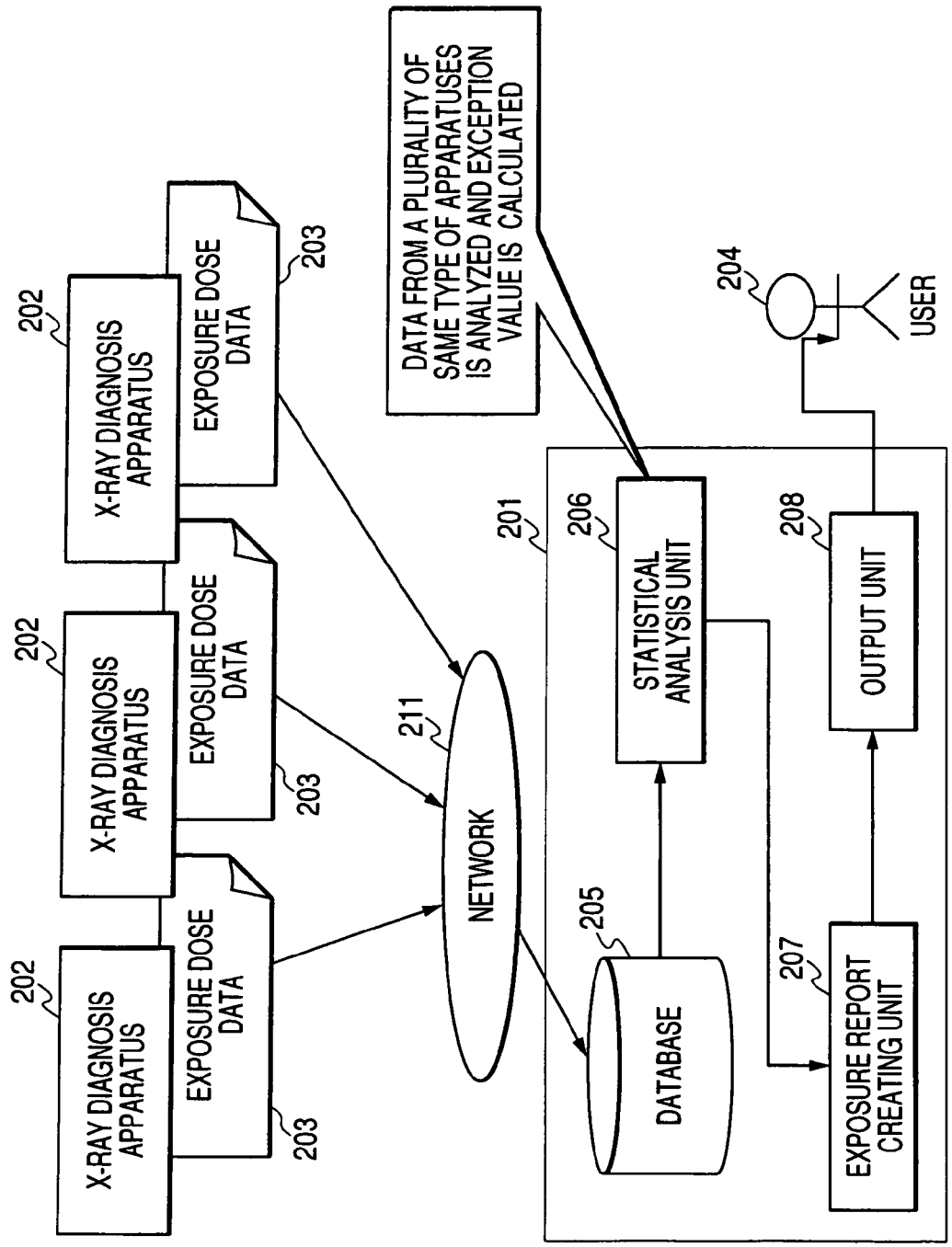
FIG. 23 is a diagram illustrating another structure of the network of FIG. 21.
Figure 24:
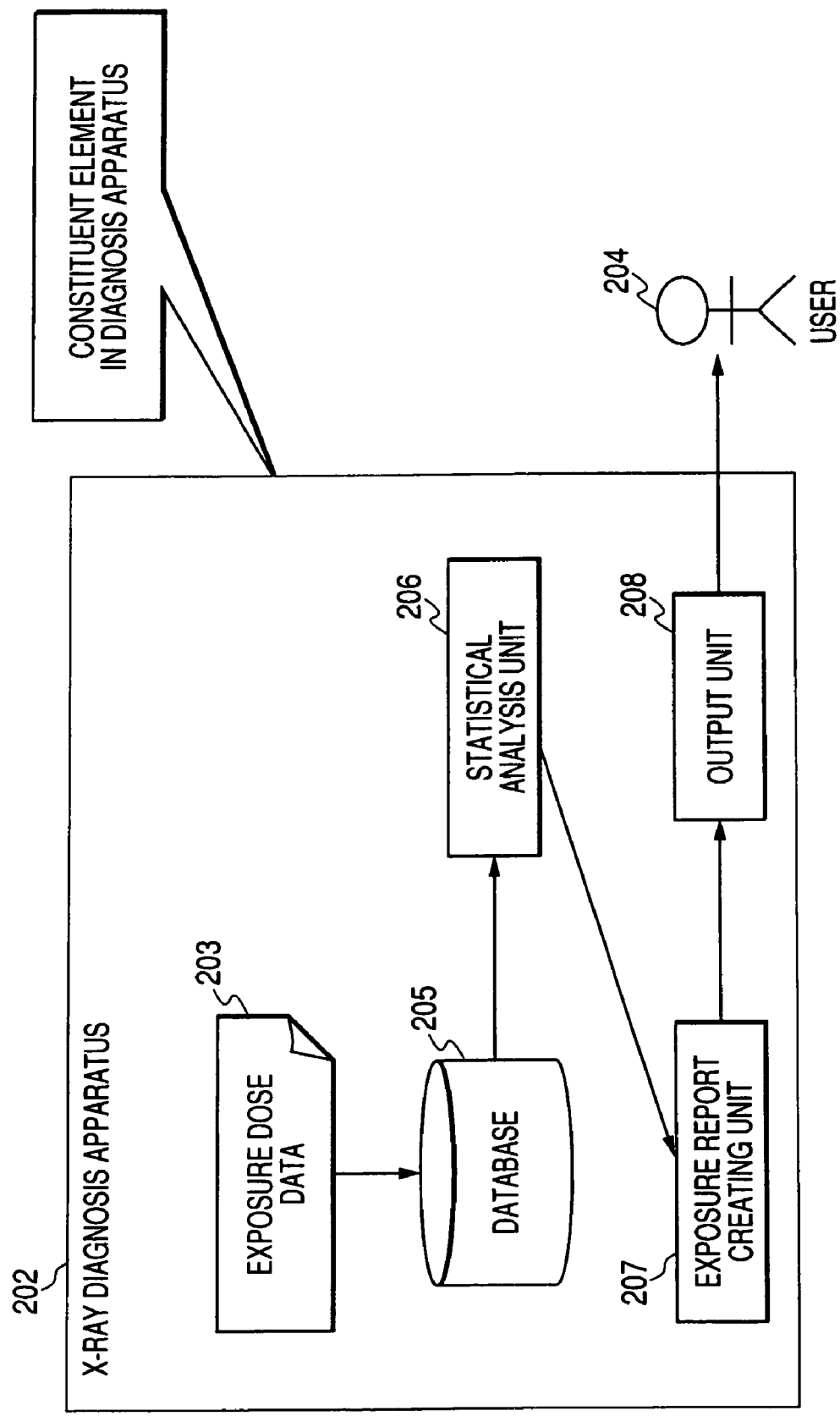
FIG. 24 is a diagram illustrating the structure of an X-ray diagnosis apparatus including the data ANALYZING CENTER 13 of FIG. 21.

As shown in FIG. 21, an X-ray exposure dose analyzing system 201 can be connected to one or a plurality of X-ray diagnosis apparatuses 202 in various manners because of the difference in the range of the analysis object. As shown in FIG. 22, the X-ray exposure dose analyzing system 201 is connected to one X-ray diagnosis apparatus 202 through a network 210 using various line systems such as the LAN, WAN and Internet lines. In addition, as shown in FIG. 23, the X-ray exposure dose analyzing system 201 is connected to a plurality of X-ray diagnosis apparatuses 202 through a network 210 using various line systems such as the LAN, WAN and Internet lines. The plurality of X-ray diagnosis apparatuses 202 may be arranged in one hospital and may be separately arranged in a plurality of hospitals. As shown in FIG. 24, the X-ray exposure dose analyzing system 201 may be assembled into the X-ray diagnosis apparatus 202.

As shown in FIG. 21, the X-ray exposure dose analyzing system 201 receives the exposure dose data from the X-ray diagnosis apparatus 202 or a RIS. The exposure dose data includes an exposure dose item, an examination protocol item, an examination part item, and a patient information item. The exposure dose item includes an effective X-ray tube current time product (mAs), CTDI, DLP, and an effective exposure dose (mSv). The examination protocol item is typically classified into a scan condition, a reconstruction condition, an exposure dose condition, and a contrast medium injection condition. The scan condition includes a scanner (stand) type, a scan part (TOMOGRAPHY part), a scan length, a scan direction, an X-ray tube voltage, an X-ray tube current, a scan time (time required per one rotation), a TOMOGRAPHY slice thickness, the number of sheets of the TOMOGRAPHY slices, a scan pitch, and a total scan time. The reconstruction condition includes a reconstruction algorithm type, a reconstruction filter, a reconstruction slice thickness, a reconstruction slice interval, the number of total images, a window width, and a window level. The patient information item includes general information such as a full name, a sex, an age, a weight, a height, and a medical history.

Figure 25:
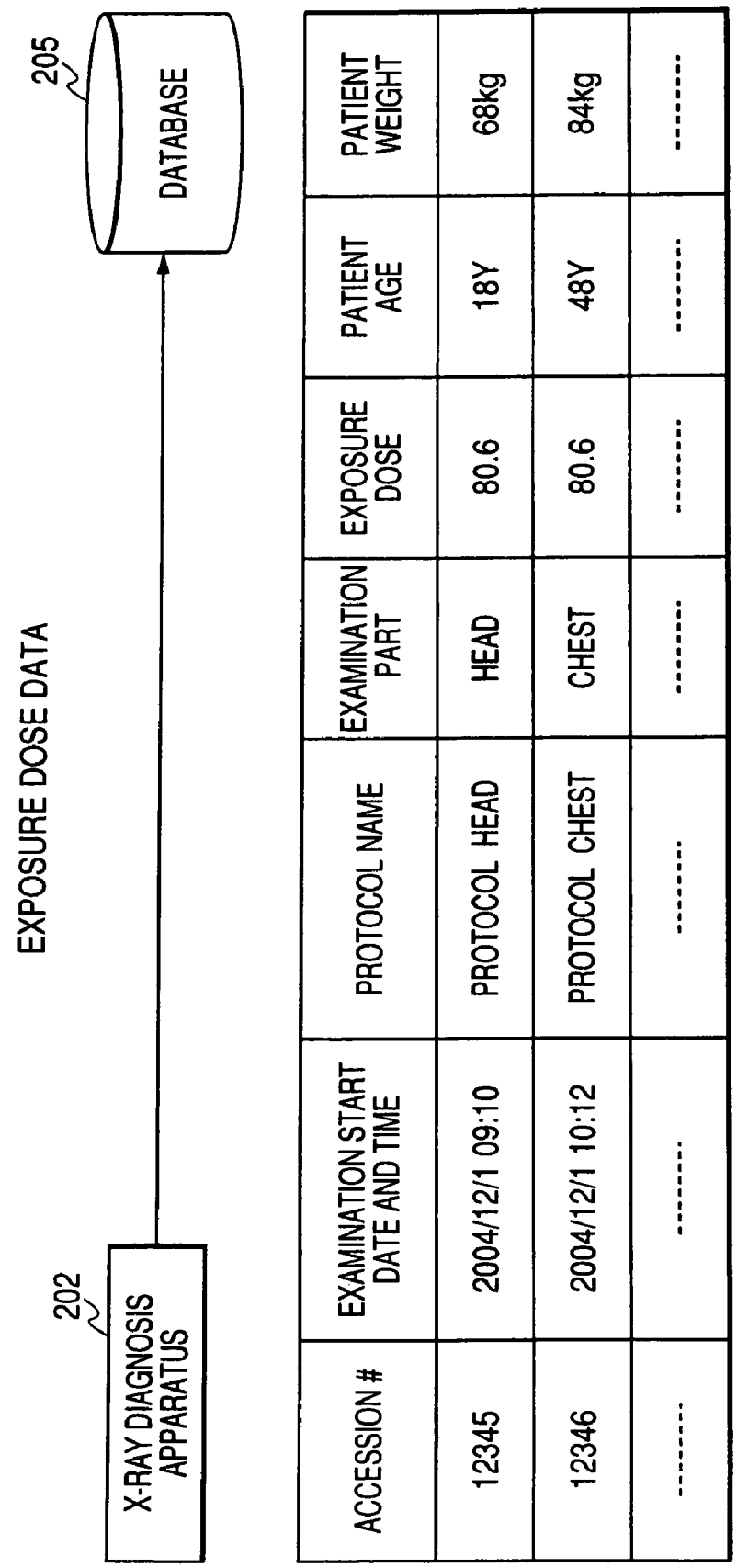
FIG. 25 is a diagram illustrating the structure of database of a database system of FIG. 21.

The database system 205 of the X-ray exposure dose analyzing system 201 stores the database of the exposure dose data illustrated in FIG. 25. The database of the exposure dose data mainly includes an accession number item corresponding to an order number generated for each examination in the radiology information system (RIS), an examination start date and time item, a protocol name item, an examination part item, an exposure dose (effective X-ray tube current time product (mAs), CTDI, DLP, or an effective exposure dose (mSv)) item, a patient age item and a patient weight item.

Figure 31:
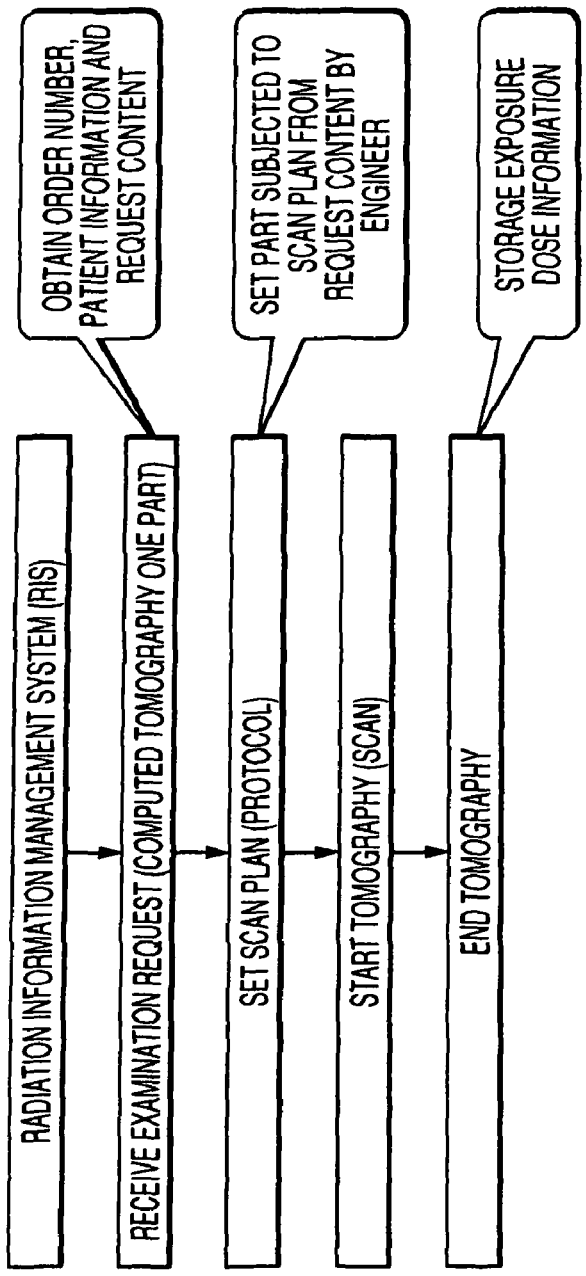
FIG. 31 is a diagram illustrating an examination flow in the first embodiment.
Figure 32:
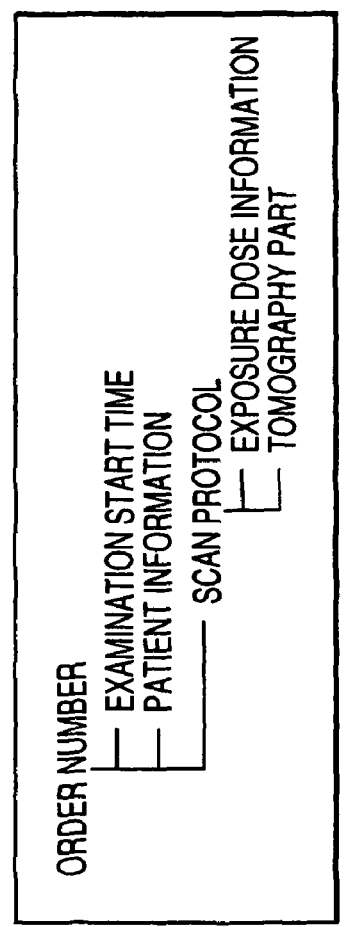
FIG. 32 is a diagram illustrating an item contained in order information of FIG. 31.
Figure 33:
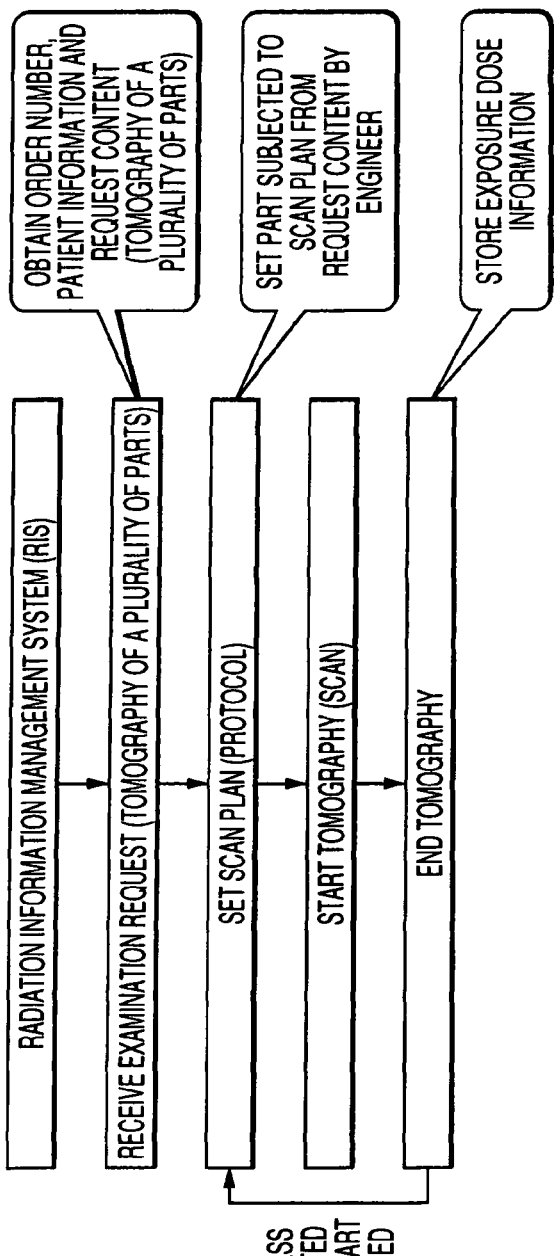
FIG. 33 is a diagram illustrating another examination flow in the first embodiment.
Figure 34:
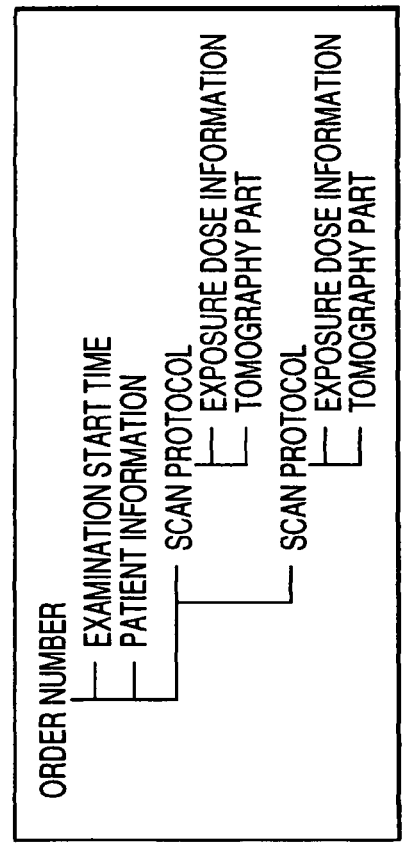
FIG. 34 is a diagram illustrating an item contained in order information of FIG. 33.

As shown in FIGS. 31 and 33, in the examination flow, when the examination is requested, the order information is generated in the radiology information system (RIS). As shown in FIGS. 32 and 34, the order number is associated with an examination start time, patient information and scan protocol information. The scan protocol information includes the exposure dose information and the TOMOGRAPHY information. The exposure dose information is generated in the RIS and the X-ray diagnosis apparatus when the TOMOGRAPHY is completed. The database system 205 has a database management system for creating a record for each examination from the data supplied from the RIS or the X-ray diagnosis apparatus to construct the database.

In addition, in the database, the accession number and the examination start date and time associated with the accession number are collectively called one process unit, that is, 'a record'. Basically, the record is created for each examination and the examination and the record have a one to one relationship. Of course, there is an exceptional relationship. However, for convenience sake, it is assumed that the record is created for each examination and the examination and the record have a one to one relationship.

Figure 28:
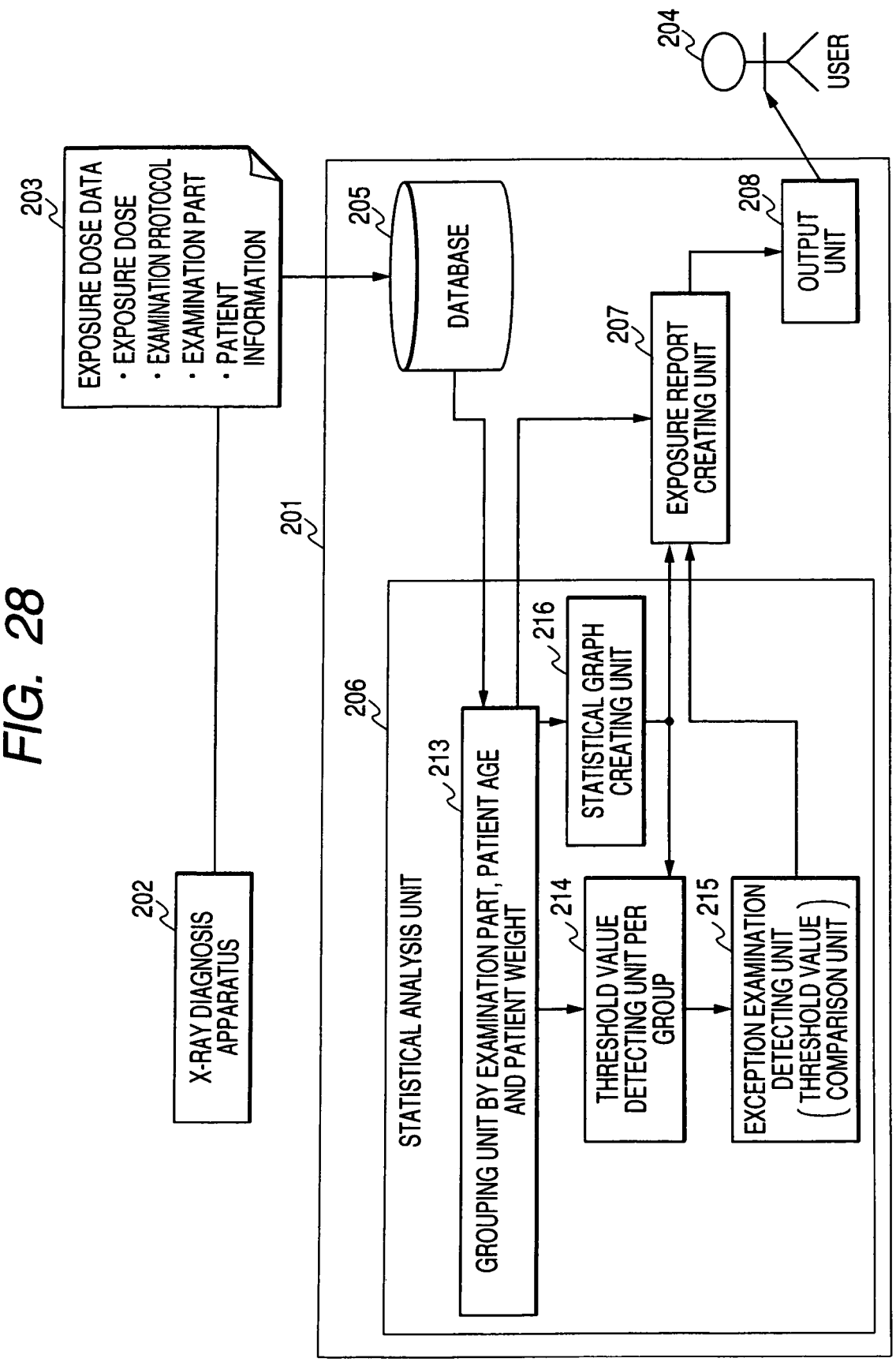
FIG. 28 is a diagram illustrating an example of a statistical analysis unit of FIG. 21.

The statistical analysis unit 206 is provided for analyzing the database of the exposure dose data statistically. As shown in FIG. 28, the statistical analysis unit 206 includes a grouping unit 213, a threshold value detecting unit 214, an exception value examination detecting unit 215, and a statistical graph creating unit 216. The grouping unit 213 classifies all the records of the database of the database system 205 according to the classification conditions to narrow the range of the analysis object record (exception value extraction object record).

The classification condition is set to every each item of the examination start date and time, the protocol name, the examination part, the age and the weight. For example, 'not designated' is set with respect to the 'examination start date and time', 'not designated' is set with respect to the 'protocol name', an 'abdomen' is set with respect to the 'examination part', the '5 to 10 years' is set with respect to the 'age', and 'not designated' is set with respect to the 'weight'. By these classification conditions, the record of the abdomen examination with respect to the patient who is 5 to 10 years old is extracted from the database.

In addition, it is possible to optionally designate the analysis period (exception value monitoring period) using the 'examination start date and time' item. In general, the analysis is repeated and changed every a constant restriction period such as three months according to the exposure report creating period. For convenience sake, 'the latest three months' are set with respect to the 'examination start date and time'. In addition, in an example of FIG. 23, it is possible to add the 'X-ray diagnosis apparatus type' to the classification condition. As a result, it is possible to analyze the record of the same type of apparatus.

The threshold value detecting unit 214 determines the threshold value to specify the exception value based on the exposure dose distributions for the plurality of records extracted from the grouping unit 213. The exposure dose distribution is created by the statistical graph creating unit 216. The threshold value detecting unit 214 may determine the threshold value to specify the exception value based on the exposure dose distributions for the plurality of records narrowed by the condition (threshold value determining condition) different from the condition for narrowing the analysis object record (analysis object narrowing condition). In general, in the threshold value determining condition, among the analysis object narrowing conditions, the analysis period (exception value monitoring period) using the 'examination start date and time' item is different and the condition items other than the analysis period are the same. For example, it is determined whether the exception value examination exists or not for the examinations for the latest three months or not and the threshold value for performing the determination is determined from the exposure doses of the examinations for the latest twelve months. As a result, the threshold value error due to the data shortage can be reduced.

Figure 29:
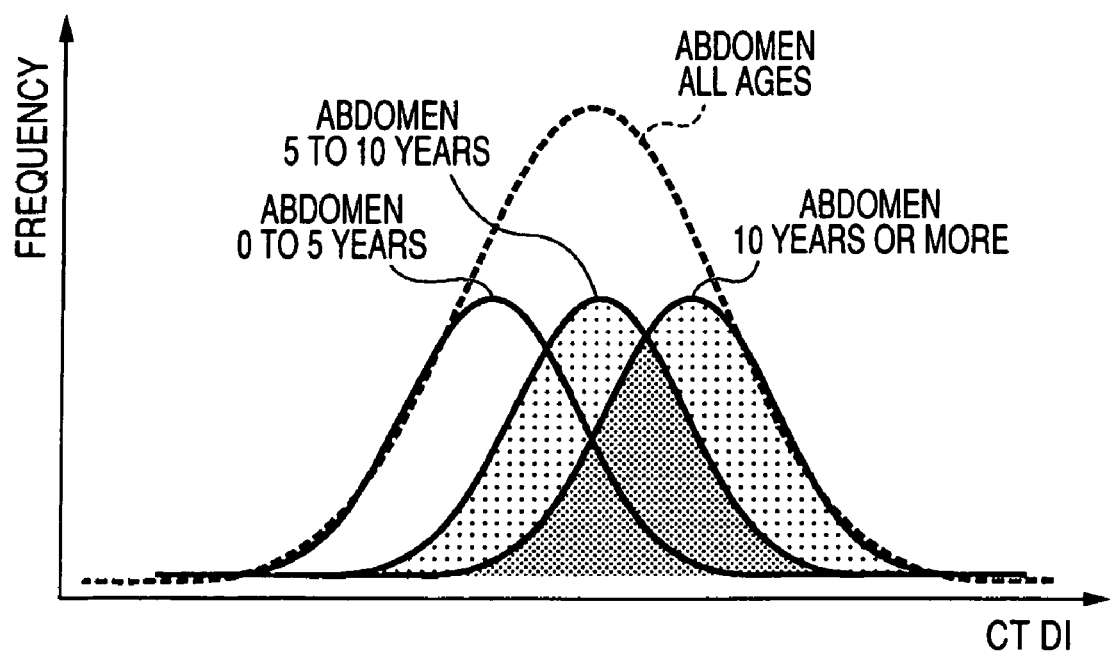
FIG. 29 is a diagram illustrating an example of a statistical graph created by a statistical graph creating unit of FIG. 28.

For example, as shown in FIG. 29, the exposure dose distribution in which a horizontal axis indicates exposure dose and a vertical axis indicates, as a frequency, the variation of the frequency (the number of the examinations and the number of the records) with respect to the exposure dose. For example, the threshold value is determined according to a value obtained by multiplying the difference between the exposure doses of the examinations located in the high level 25% of the overall frequencies and the exposure doses of the examinations located in the low level 25% of the overall frequencies by 1.5. The exception value examination detecting unit 215 detects the exposure dose higher than the threshold value as the exception value. The exception value examination detecting unit 215 extracts the examination (record) having the exposure dose higher than the threshold value as the exception examination.

Figure 30:
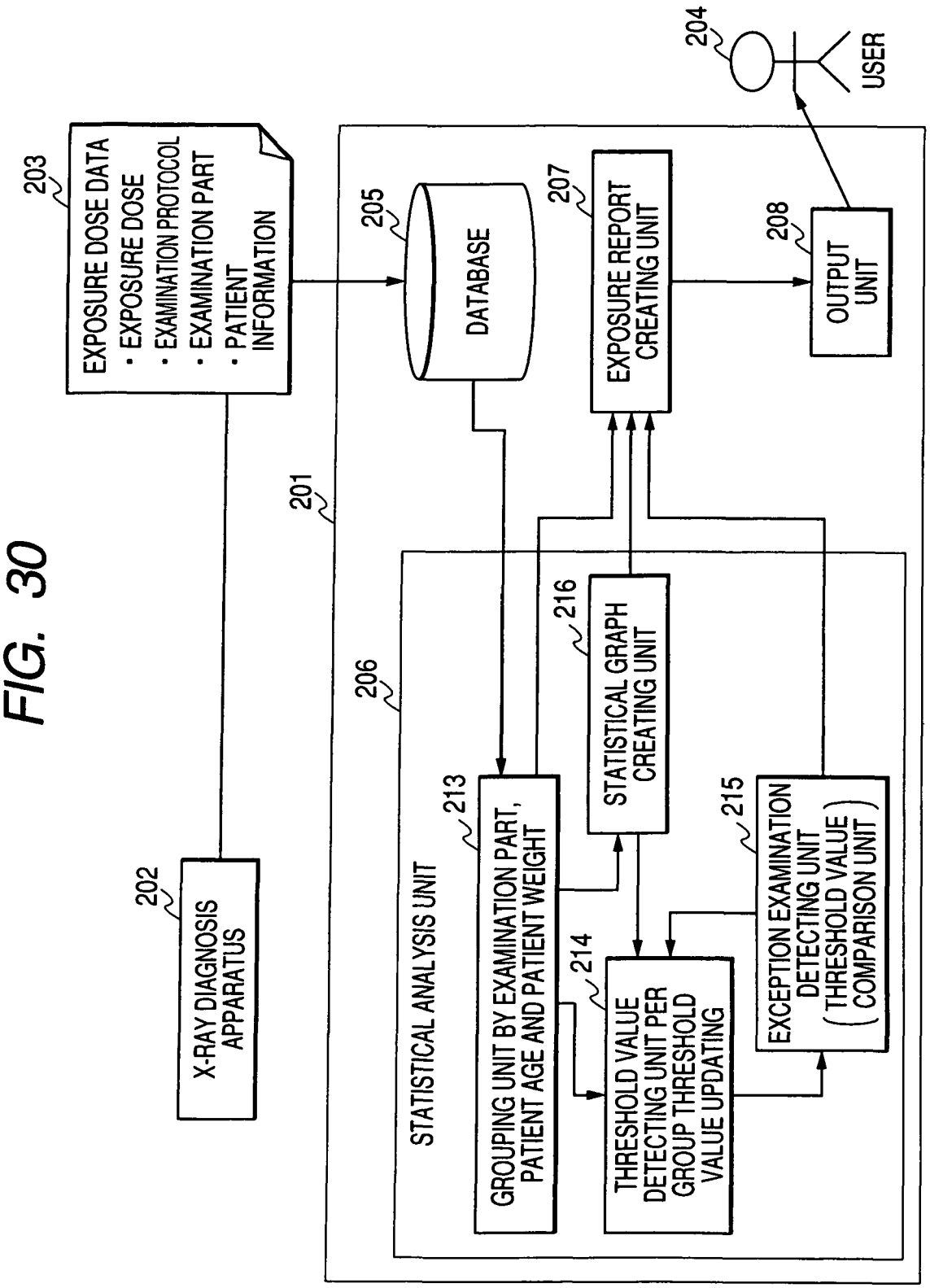
FIG. 30 is a diagram illustrating another structure of the statistical analysis unit of FIG. 21.

In addition, as shown in FIG. 30, the threshold value detecting unit 214 may determine the threshold value again from the exposure dose distributions for the plurality of records excluding the exception examination (exception record) (updating threshold value). The processes for the exclusion of the exception examination (exception record) and the determination of the threshold value may be repeated by the predetermined times. In general, by repeating the processes for the exclusion of the exception examination (exception record) and the determination of the threshold value two times, it is possible to specify the exception examination with high accuracy. In addition, the processes of the exclusion of the exception examination (exception record) and the determination of the threshold value may be repeated until the regular check is cleared.

The exception value examination detecting unit 215 detects the exposure dose higher than the threshold value as the exception value. The exception value examination detecting unit 215 extracts the examination (record) having the exposure dose higher than the threshold value as the exception examination. The exception value examination detecting unit 215 supplies the extracted exception examination to the exposure report creating unit 207.

Figure 26:
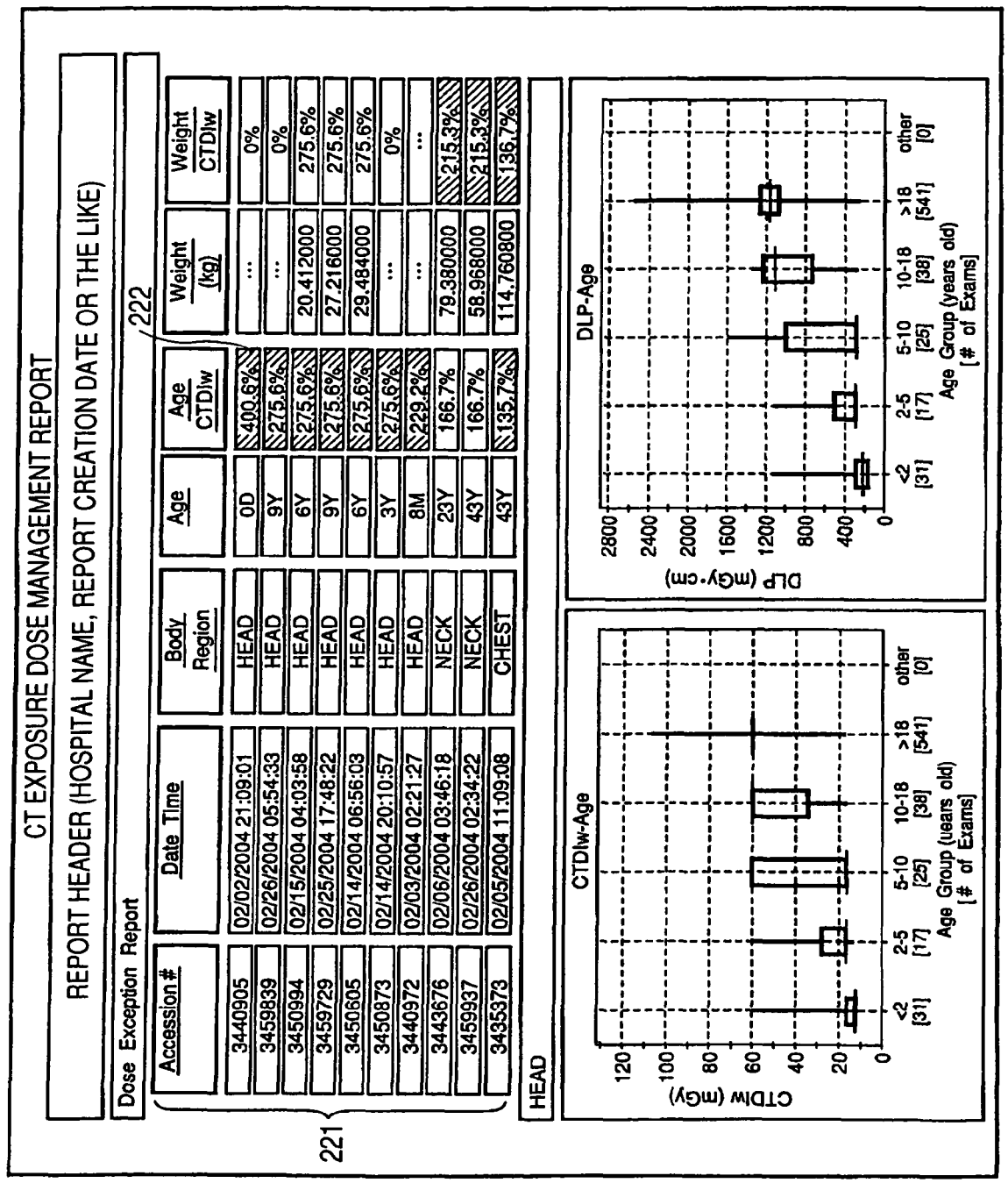
FIG. 26 is a diagram illustrating an example of a report created by an exposure report creating unit of FIG. 21.

The exposure report creating unit 207 is supplied with a plurality of examination record data extracted in the grouping unit 213 as the analysis object (report object), accession number data of the plurality of exception examinations extracted in the exception value examination detecting unit 215, the exposure dose distribution data of FIG. 29 created by the statistical graph creating unit 216, and data necessary for creating the exposure report, such as the graph data illustrated in FIG. 7 created by the statistical graph creating unit 216. The exposure report creating unit 207 creates the exposure report illustrated in FIG. 26. The exposure report 209 created by the exposure report creating unit 207 is generally output to the user 204 from the output unit 208 serving as the server unit.

Figure 27:
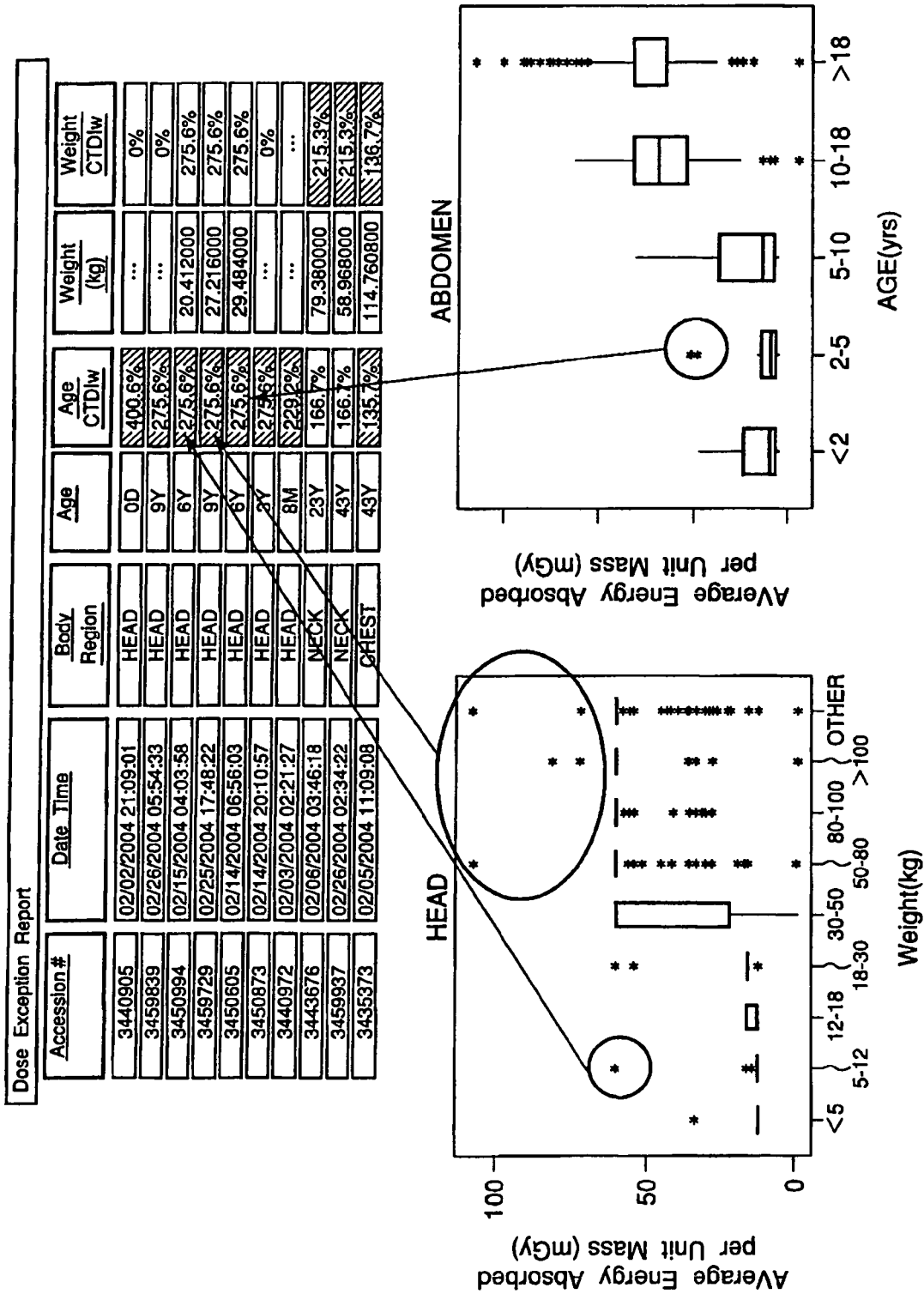
FIG. 27 is a diagram illustrating distribution of an exception value of the report of FIG. 21.

The analysis object record 221 is listed in the exposure report (exposure dose management report). The exception value 222 of the listed record 221 is displayed with the unusual type, that is, the different character color or background color from a normal value. The analysis object record 221 is listed in the exposure report (exposure dose management report). This report includes a record list, the graph of FIG. 7 and the distribution of FIG. 29. As shown in FIG. 27, the exception value may be plotted in the graph of FIG. 7.

According to the present embodiment, the records (examinations) stored in the database system 205 are classified into a plurality of groups according to any condition and the analysis is performed for each group. The classification condition includes an examination time, an examination part, an age, a weight or the like. Since the analysis is performed for each group, the tendency of the exposure dose for every group can be reflected. As a result, it is possible to improve the analysis quality. Specifically, the determination accuracy of the exception value can be improved. Therefore, it is possible to improve the examination quality.

Second Embodiment

Figure 35:
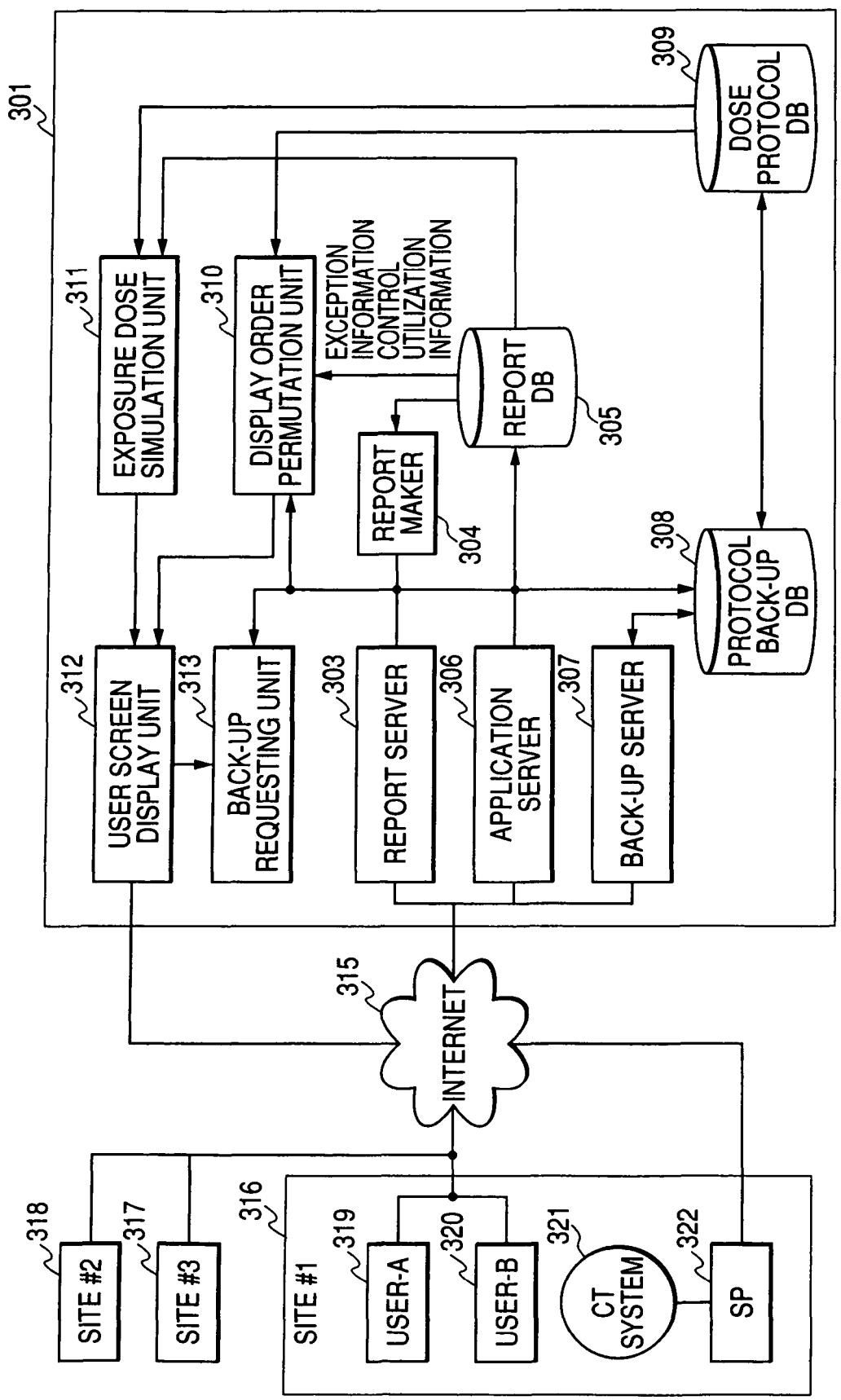
FIG. 35 is a diagram illustrating the structure of an examination protocol distribution system according to a second embodiment.

FIG. 35 shows the structure of an examination protocol distribution system according to a second embodiment of the present invention. The examination protocol distribution system 301 is connected to client information terminals 319 and 320 such as workstations arranged in a plurality of medical sites (mainly, hospital or medical research institute) 316, 317, and 318 through electronic communication lines 315 such as an Internet and is connected to a service processor 322 of a CT system (X-ray TOMOGRAPHY apparatus) 321 serving as the radiation diagnosis apparatus.

The examination protocol distribution system 1 mainly serves to distribute the exposure dose report (exposure report) and the examination protocol list to the client side terminals 319 and 320. In order to accumulate the information necessary for creating the distribution information, the examination protocol distribution system 301 includes a report database system 305, a protocol back-up database system 308 for accumulating the data of the examination protocols used in each hospital and an exposure dose protocol database system 309.

The report database system 305 accumulates the data (for example,. CTDIw and DLP) corresponding to the exposure dose for each radiation examination that an application server 306 receives from the service processors 322 of the plurality of radiation diagnosis apparatuses 321 provided in the plurality of hospital sites 316 to 318. The database of the report database system 305 is composed of a plurality of records respectively corresponding to the plurality of radiation examinations, similarly to the database 205 according to the first embodiment. Each record includes an order number generated in a radiology information system (RIS) for each examination, an examination start date and time item, an examination protocol, an examination object, an examination part, an exposure dose (an effective X-ray tube current time product (mAs), CTDI, DLP, or an effective exposure dose (mSv)), a patient's age and a patient's weight.

A protocol back-up database system 308 accumulates examine protocol data used in each radiation diagnosis apparatus 321 that a back up server 307 receives from the service processors 322 of the plurality of radiation diagnosis apparatuses 321, according to the back up request of a back up request unit 313.

Figure 46:
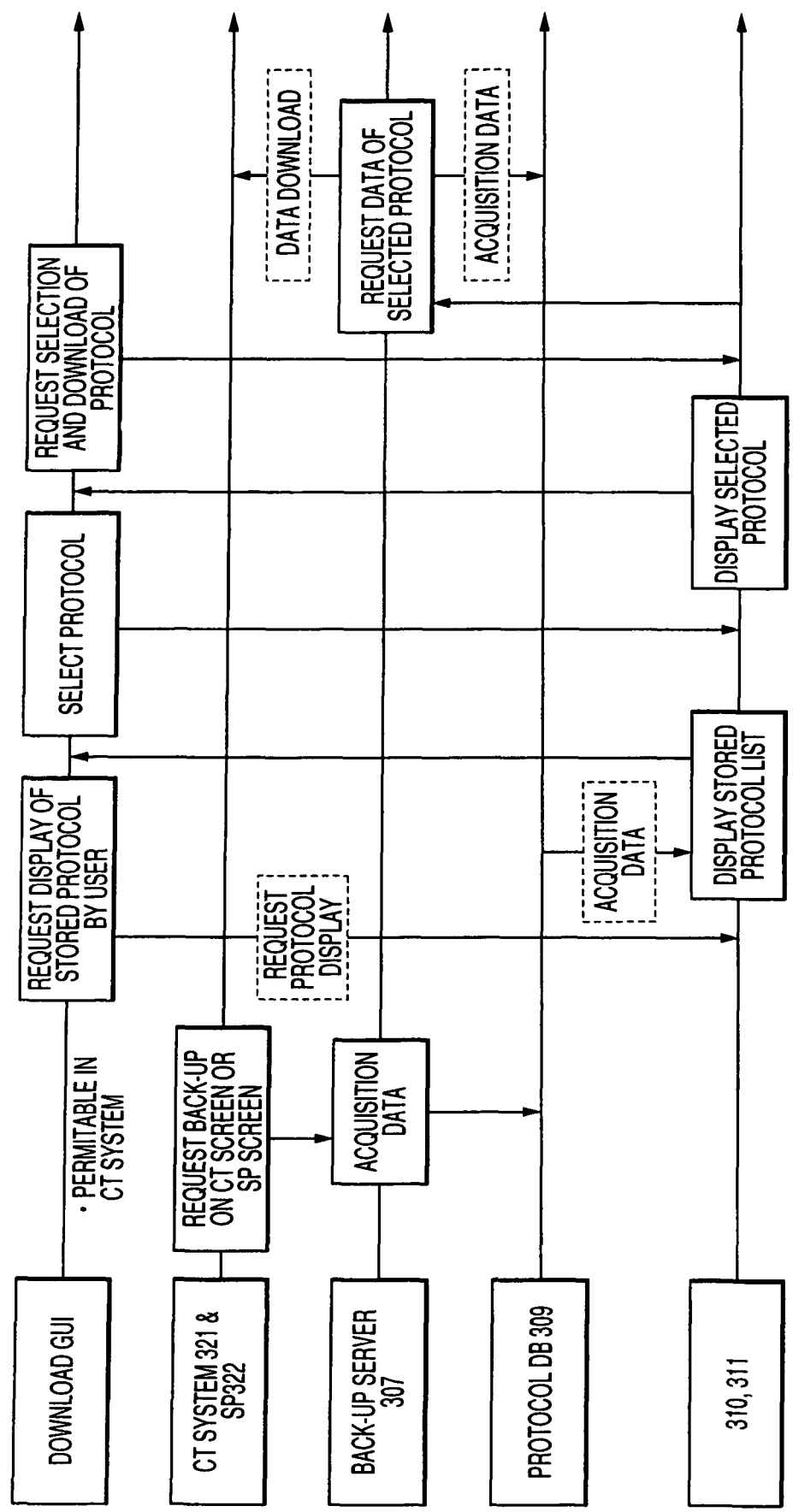
FIG. 46 is a diagram illustrating a modified example of FIG. 36.

As shown in FIG. 46, with regard to the use of the backed-up examination protocol, when the user requests the back up on the screen of the CT system 321 or the screen of the service processor 322, the examination protocol data in the CT system 321 is stored in the protocol back-up database system 308 through the back up server 307. After that, when the request of the examination protocol display is received from the user through the terminals 319 and 320, according to the user ID and the request content, the back up server 307 acquires the examination protocol data for the corresponding CT system 321 from the protocol back-up database system 308, creates the protocol list and transmits the created protocol list to the terminals 319 and 320. When a desired protocol is selected from the protocol list by the user so that the downloading of the protocol is requested, the back up server 307 transmits the data of the corresponding protocol stored in the protocol back-up database system 308 to the CT system 321 or the SP 322. Whether the downloading is made or not is determined according to a service contract with the user.

Here, the examination protocol is a set of various conditions necessary for a series of work progress of the radiation examination reaching from the TOMOGRAPHY (data collection) to the signal process (image reconstruction) and is generally classified into a scan condition, a reconstruction condition, an exposure dose condition, and a contrast medium injection condition. The scan condition includes a scanner (stand) type, a scan part (TOMOGRAPHY part), a scan length, a scan direction, an X-ray tube voltage, an X-ray tube current, a scan time (time required per one rotation), a TOMOGRAPHY slice thickness, the number of sheets of the TOMOGRAPHY slices, a scan pitch, and a total scan time. The reconstruction condition includes a reconstruction algorithm type, a reconstruction filter, a reconstruction slice thickness, a reconstruction slice interval, the number of total images, a window width, and a window level. The exposure dose condition includes an effective X-ray tube current time product (mAs), CTDI, DLP, and an effective exposure dose (mSv)). The contrast medium condition includes a contrast medium type, concentration, a dosage, an injection speed, and a scan start direction. In addition, superior examination protocols (hereinafter, referred to as a recommendation examination protocol) that the exposure dose is lower than the predetermined value (the upper limit of the dose) among the examination protocols accumulated in the protocol back-up database system 308 are selectively accumulated in a dose protocol database system 309 for control of the back up server 7.

A report maker 304 regularly collects data, which is accumulated in the report database system 305 and corresponds to the exposure dose for every radiation examination by the plurality of radiation diagnosis apparatuses 321, for each radiation diagnosis apparatus 321 or each hospital and creates the exposure dose report. The report server 303 distributes the exposure dose report created by the report maker 304 to the corresponding client terminals 319 and 320, respectively. A display order permutation unit 310 creates the list of a plurality of recommendation examination protocols that at least one of the examination object part and the examination object is the same with respect to the specific examination protocol showing high frequency of usage or exceptionally high exposure dose from the plurality of examination protocols accumulated in the exposure protocol database system 309.

In addition, whether the exposure dose has an exceptionally high value (exception value) or not is generally determined through the threshold value comparison, similarly to the first embodiment. Specifically, the threshold value is determined so as to specify the exception value based on the exposure dose distributions for the plurality of extracted records.

An exposure dose simulation unit 311 simulates the exposure dose according to the recommendation examination protocol or the examination protocol arbitrarily designated by the user. A user screen display unit 312 constructs the respective screens based on the recommendation examination protocol list created by the display order permutation unit 310 or the simulation result by the exposure dose simulation unit 311 and distributes the respective screen data to the client side terminals 319 and 320.

Figure 36:
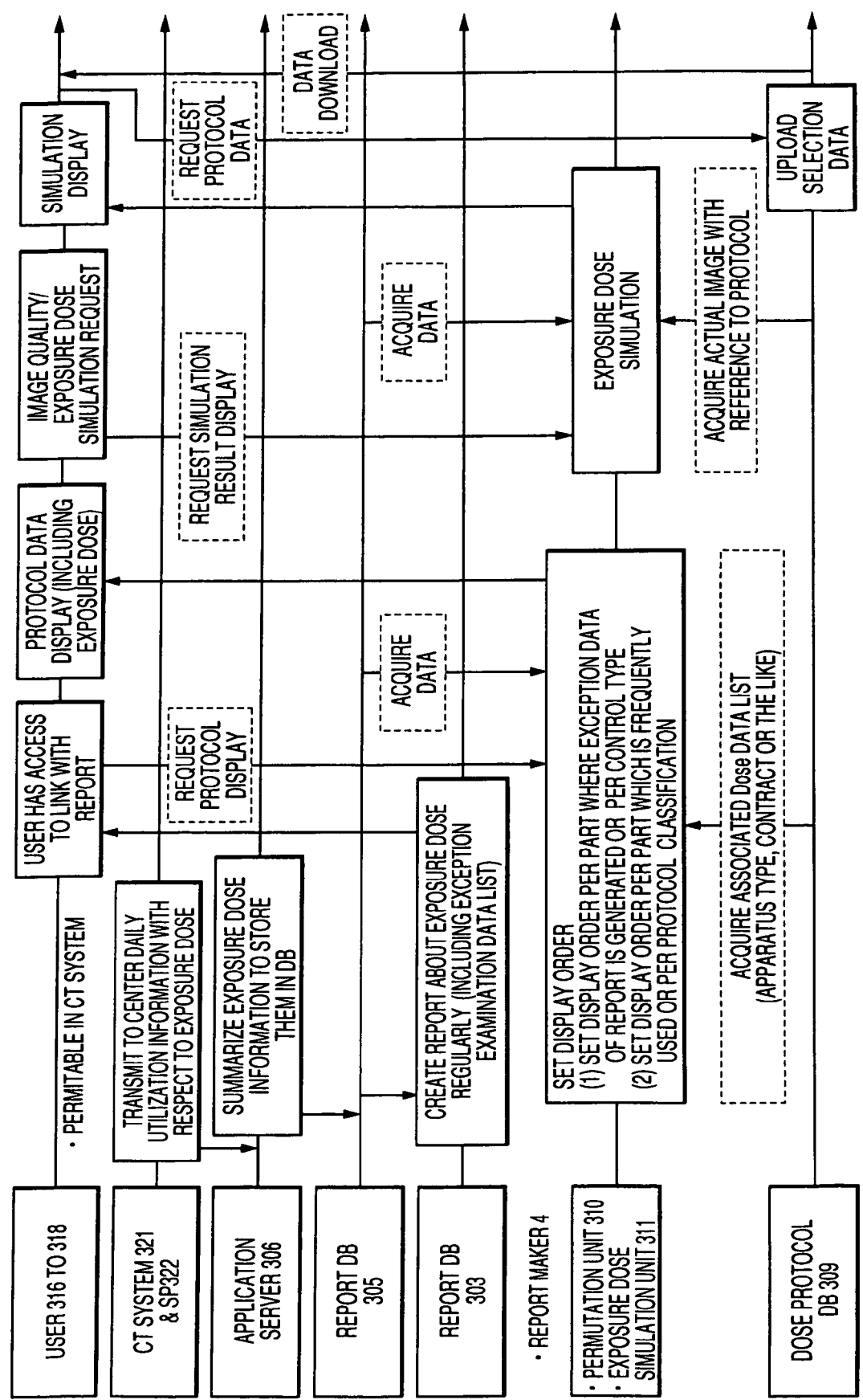
FIG. 36 is a diagram illustrating a sequence of an examination protocol distribution according to the second embodiment.

FIG. 36 shows a sequence of the examination protocol distribution by the examination protocol distribution system 301 according to the present embodiment. The user sites 316 to 318 are provided with the radiation diagnosis apparatus represented as the CT system 321 together with the client side information terminals 319 and 320. The information for the exposure dose of the radiation examination using the CT system 321 is transmitted from the CT system 321 to the application server 306 of the examination protocol distribution system 301 through the service processor 322 and is accumulated in the report database system 305. In the examination protocol distribution system 301, the information for the exposure dose of the radiation diagnosis using the respective radiation diagnosis apparatuses 321 is collected from the plurality of sites 316, 317, and 318 and is stored in the report database system 305. The radiation diagnosis apparatus may be an X-ray diagnosis apparatus and a nuclear medicine apparatus as well as the CT system. In addition, it is not prevented that the exposure dose information generated in the radiation diagnosis apparatus is transmitted to the application server 306 via the a picture archiving communication system (PACS) or the radiology information system (RIS). Representative examples of the information for the radiation exposure dose are the CTDIw and DLP. The information for utilization of the radiation diagnosis apparatus 21 together with the information for the exposure dose is also collected from the plurality of sites 316, 317 and 318 and is stored in the report database system 305. The information of utilization situation includes examination times, throughput of a patient, and an average examination time for every examination type.

Figure 37:
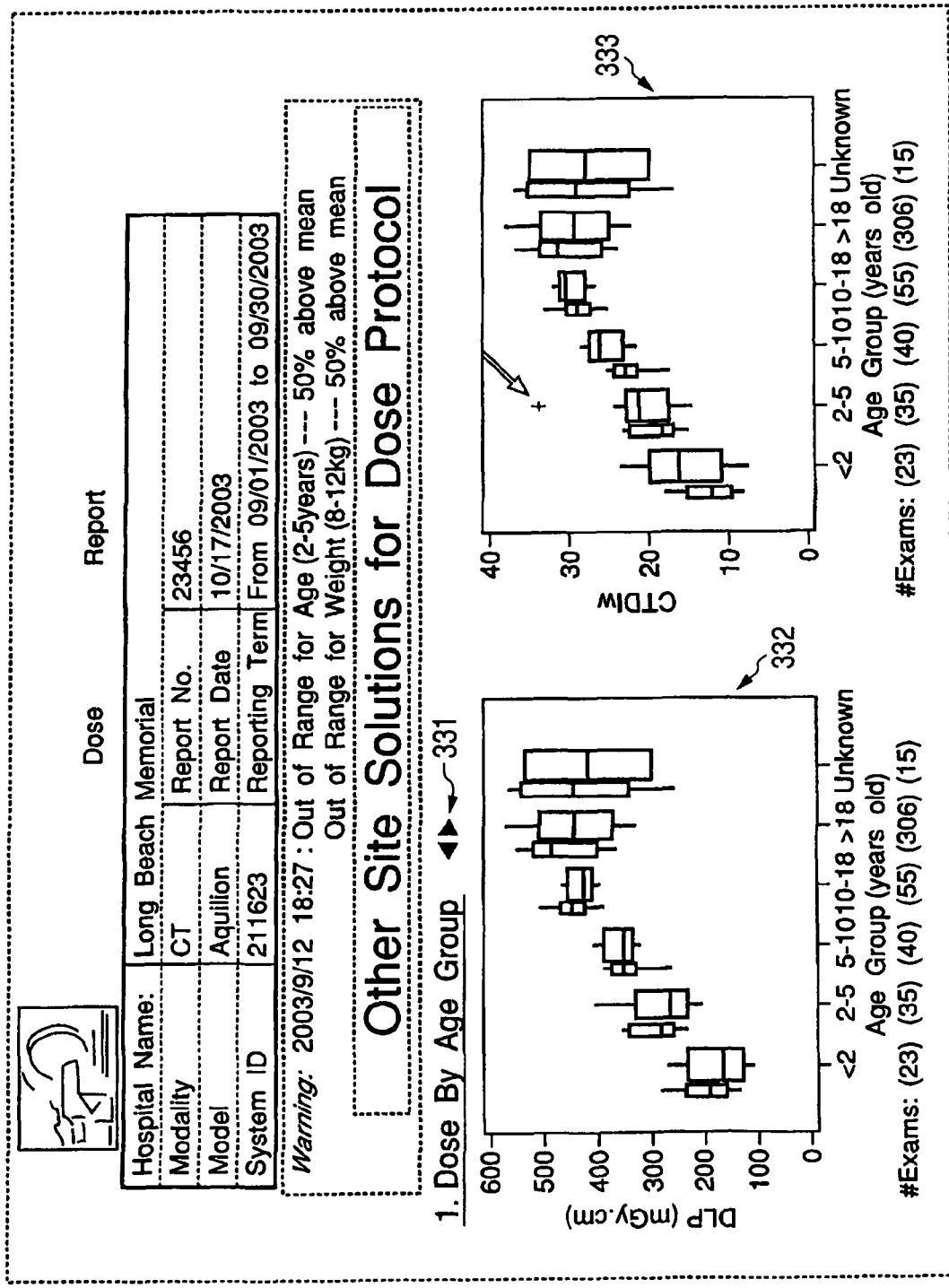
FIG. 37 is a diagram illustrating an exposure dose report in the second embodiment.
Figure 38:
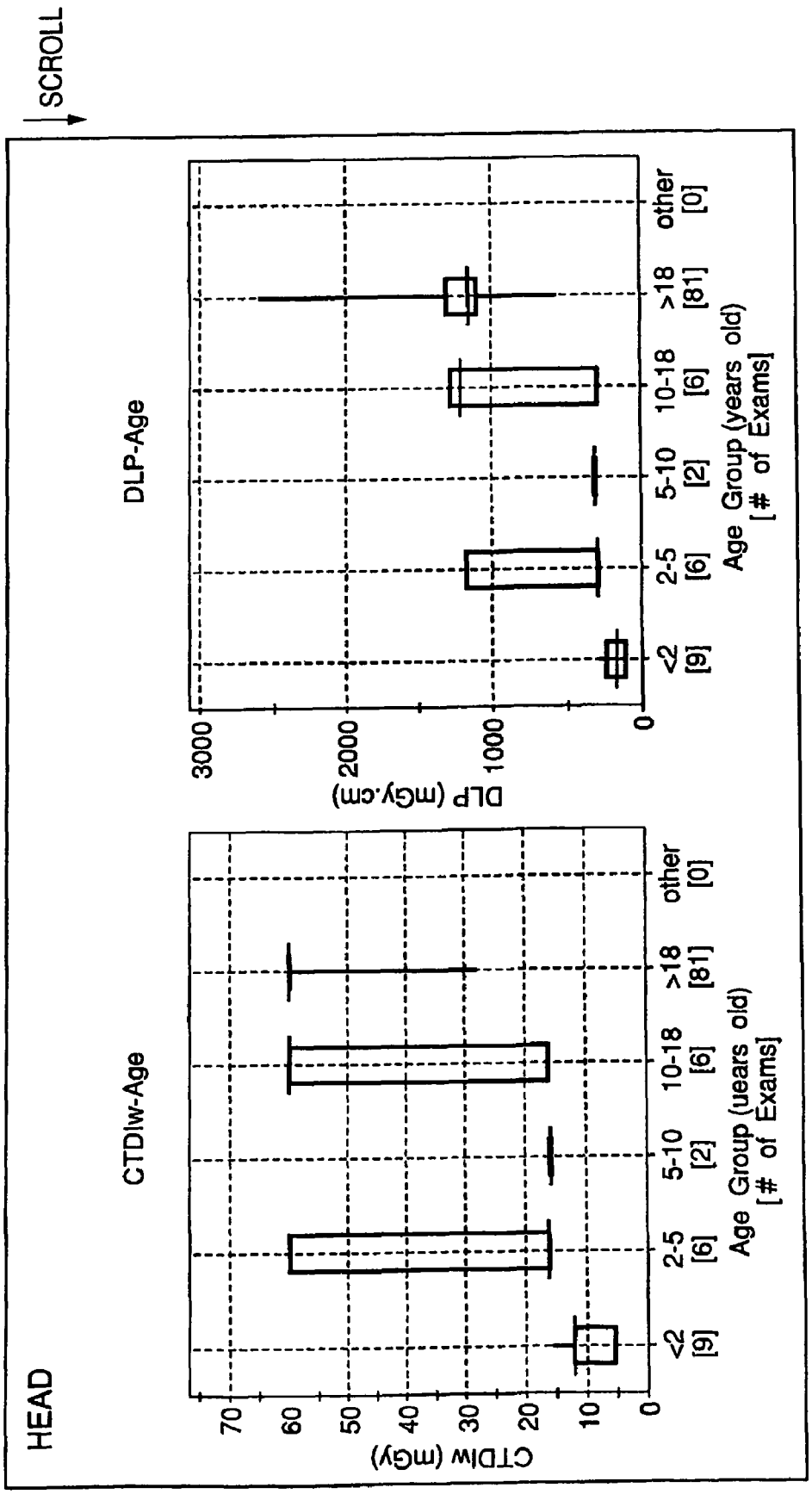
FIG. 38 is a diagram illustrating another example of tabulation in the exposure dose report of FIG. 37.
Figure 39:
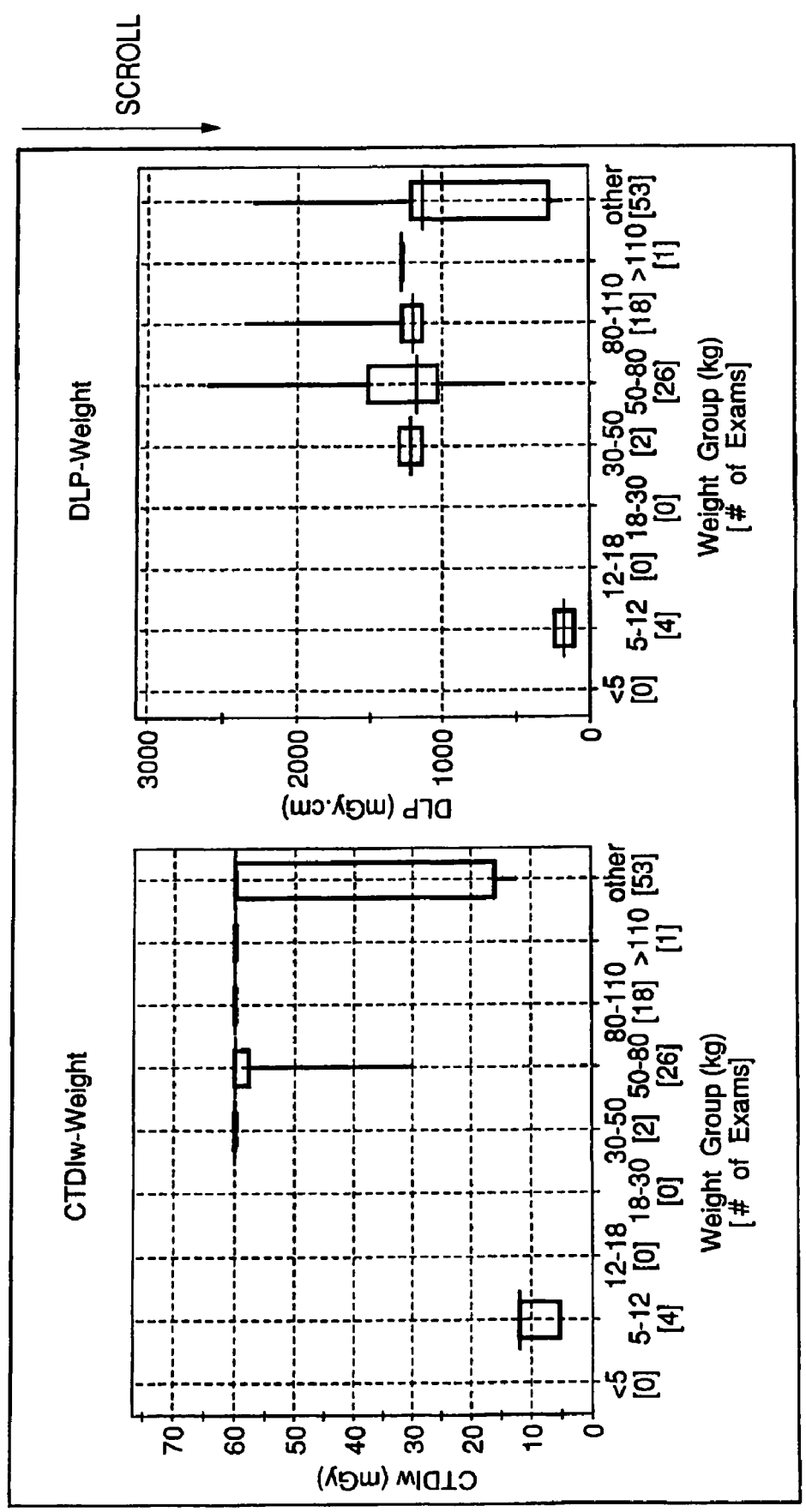
FIG. 39 is a diagram illustrating another example of tabulation in the exposure dose report of FIG. 37.
Figure 40:
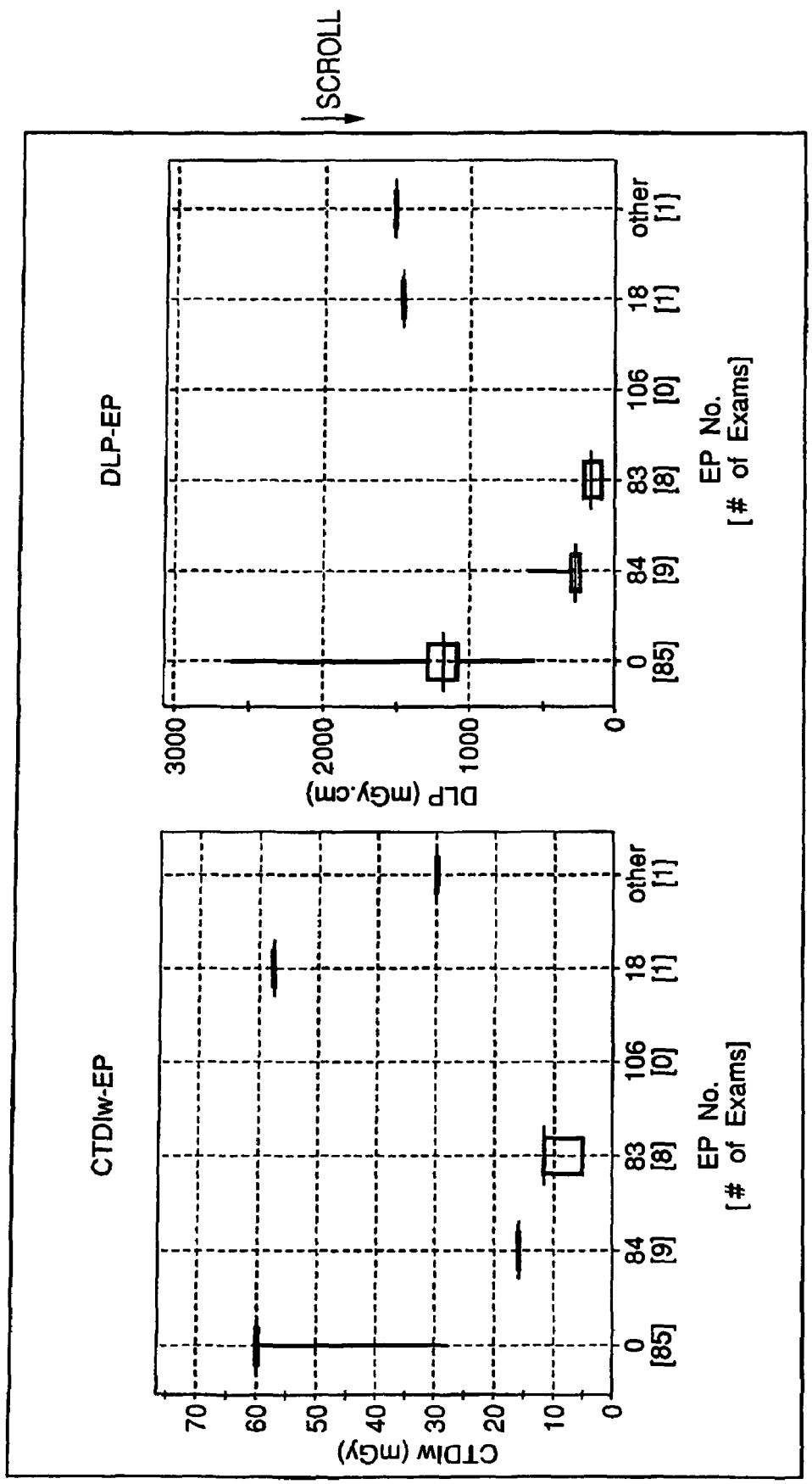
FIG. 40 is a diagram illustrating another example of tabulation in the exposure dose report of FIG. 37.

The exposure dose report is created for each radiation diagnosis apparatus 21 by the report maker 304 based on the exposure dose data and the utilization data which is generated at a regular period such as at 10:00 a.m. every Monday, that is, at the period from at 10:00 a.m. last Monday to at 10:00 a.m. this Monday and which is accumulated in the report database system 305. The exposure dose report is transmitted from the report server 303 to the client side terminals 319 and 320 corresponding to the respective radiation diagnosis apparatuses 321. The exposure data includes CTDIw and DLP and the utilization data includes a weight, an age, a disease name, an examination part, an examination code and an examination number. FIG. 37 shows the exposure dose report. In the exposure dose report, for example, the relationship between the age and the DLP 332 and the relationship between the age and the CTDIw 333 are displayed. By the scrolling, different relationships illustrated in FIGS. 38, 39 and 40 are displayed. FIG. 38 shows the relationship between the age and the DLP and the relationship between the age and the CTDIw for head examination. FIG. 39 shows the relationship between the weight and the DLP and the relationship between the weight and the CTDIw. FIG. 40 shows the relationship between the EP number and the CTDIw and the relationship between the EP number and the DLP.

When the exposure report of FIG. 37 is further scrolled down in the client terminals 319 and 320, the exception examination report for the corresponding radiation diagnosis apparatus 321 illustrated in FIG. 41 is displayed. The report is created by the report maker 304 using the data accumulated in the report database system 305 and the report is transmitted from the report server 303 to the client side terminals 319 and 320. The report includes a summary list of the radiation examination composed of items such as a TOMOGRAPHY part, an age, an exposure dose, and a weight for the radiation examinations carried out for a predetermined period. In the summary list of the radiation examination, the display aspect of the exposure dose item in the examination that the exposure dose is higher than the predetermined value is different from the display aspect in the other examinations. In addition, the message that 'when the distribution value of the examination exposure dose is checked, the value (exception value) is abnormally higher than that in the distribution state' or 'the exposure dose value (exception value) is higher than the threshold value' is displayed, if necessary. Therefore, the user can recognize the message as warning information. The examination protocol list of each examination illustrated in FIG. 42 is displayed through the scrolling of the exposure report.

Figure 43:
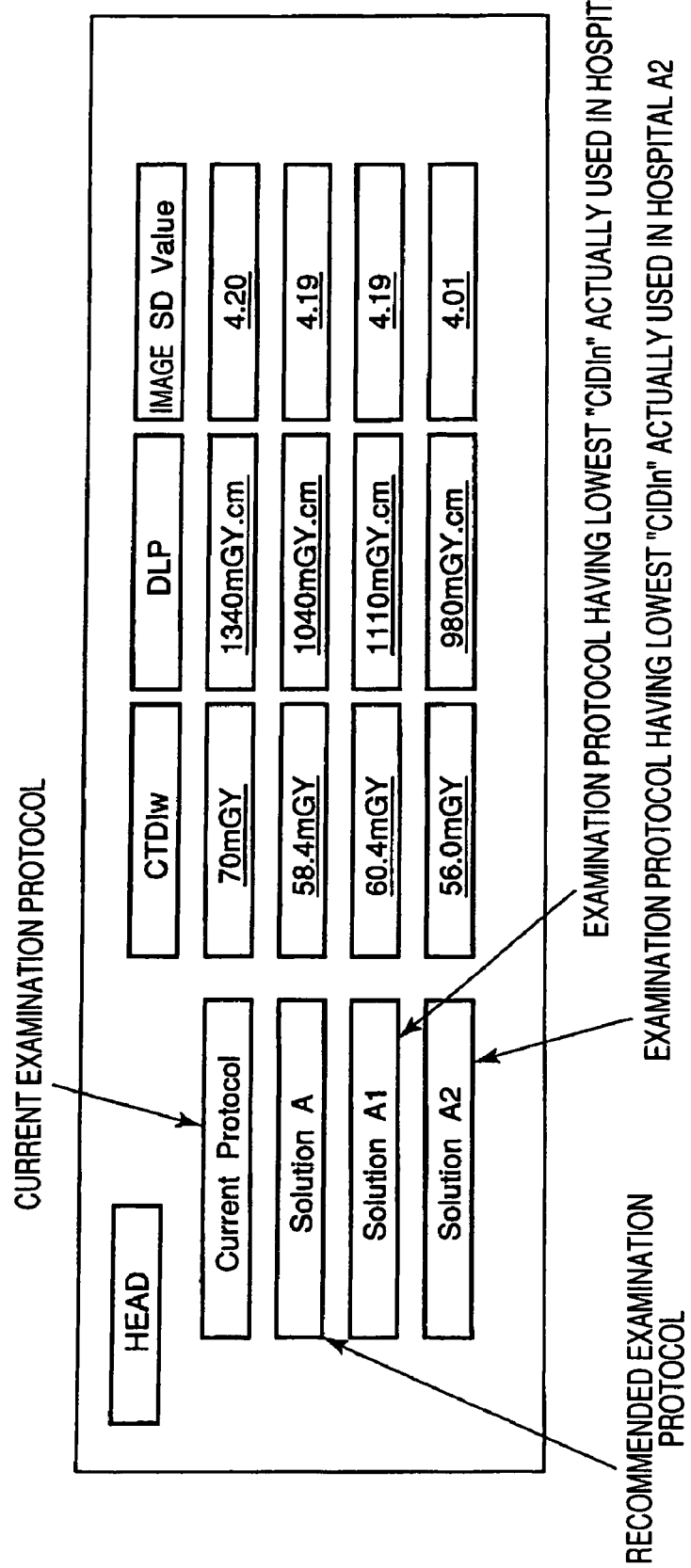
FIG. 43 is a diagram illustrating a recommendation examination protocol list distributed by clicking a [Solution A] button in an abnormal exposure dose report of FIG. 42.

In each examination of the exposure report of FIG. 41, a button 336 of a 'Solution A (or B, C)' is prepared. When the button 336 of the 'Solution A' of the examination that the exposure dose shows the exception value is clicked by the client side terminals 319 and 320, a recommendation examination protocol list illustrated in FIG. 43 is created. In the recommendation examination protocol list, the examination protocol which is the examination protocol of another hospital of which the examination object is the same with respect to the examination protocol of the clicked 'Solution A' and has a minimum CTDI as the exposure dose index for each hospital is extracted or permutated and listed according to the CTDI as the exposure dose index. In addition, in the recommendation examination protocol list, the recommendation examination protocol supplied by the apparatus maker that at least the examination object is the same with respect to the examination protocol of the clicked 'Solution A' and the examination protocol used in another hospital together with the respective exposure dose indexes (CTDI and DLP) and the image quality index (image SD) are included. The maker supplying recommendation examination protocols are previously accumulated in the exposure dose protocol database system 309 and the display permutation unit 310 selects the plurality of recommendation examination protocols of which the examination, the TOMOGRAPHY part and the examination object are the same and of which the age and the weight are approximate range. In addition, from the back up database system 8, the display permutation unit 310 searches a plurality of examination protocols of which the TOMOGRAPHY part and the examination object are the same with respect to the examination protocol of the clicked 'Solution A' and which is used in another hospital in that the age and the weight are in the approximate range. In addition, the display permutation unit 310 permutates the plurality of searched examination protocols used in another hospital as the exposure dose index for every hospital according to the CTDI. Further, the display permutation unit 310 extracts the examination protocol of which the CTDI is the lowest as the exposure dose index for every hospital and creates a list using the extracted examination protocols together with the current examination protocol and the recommendation examination protocol. The recommendation examination protocol list is transmitted to the client side terminals 319 and 320 through the user screen display unit 312 to be displayed thereon.

When the button 337 of the 'Solution A' of the summary list of the displayed recommendation examination protocol is clicked on the client side terminals 319 and 320, the detailed information of the examination protocol is transmitted from the exposure dose protocol database system 309 to the client side terminals 319 and 320 via the display order permutation unit 310 and the user screen display unit 312 and is displayed as shown in FIG. 44. For example, in the exposure report of FIG. 41, in the case where the head blood vessel contrastradiography examination includes many exposure dose examinations, the recommendation examination protocols associated with it may be preferentially displayed, the recommendation examination protocol associated with the examination protocol that the number of the examinations is large may be preferentially displayed and the recommendation examination protocol associated with the examination protocol that the average examination time is relatively long may be preferentially displayed.

To the detailed information of the recommendation examination protocol of FIG. 44, sample images obtained when tomographed with the examination protocol are attached. The data of the sample image corresponding to each recommendation examination protocol is stored in the exposure dose protocol database system 309 together with the data of the recommendation examination protocol. After that, when the downloading is requested from the client side terminals 319 and 320, the data of the selected recommendation examination protocol is downloaded in the CT system 321 via the service processor 322. In addition, the data of the selected recommendation examination protocol may be directly downloaded into the CT system 321, may be downloaded into the CT system 321 via the SP 322 and may be downloaded on the PC used by the user.

Figure 45:
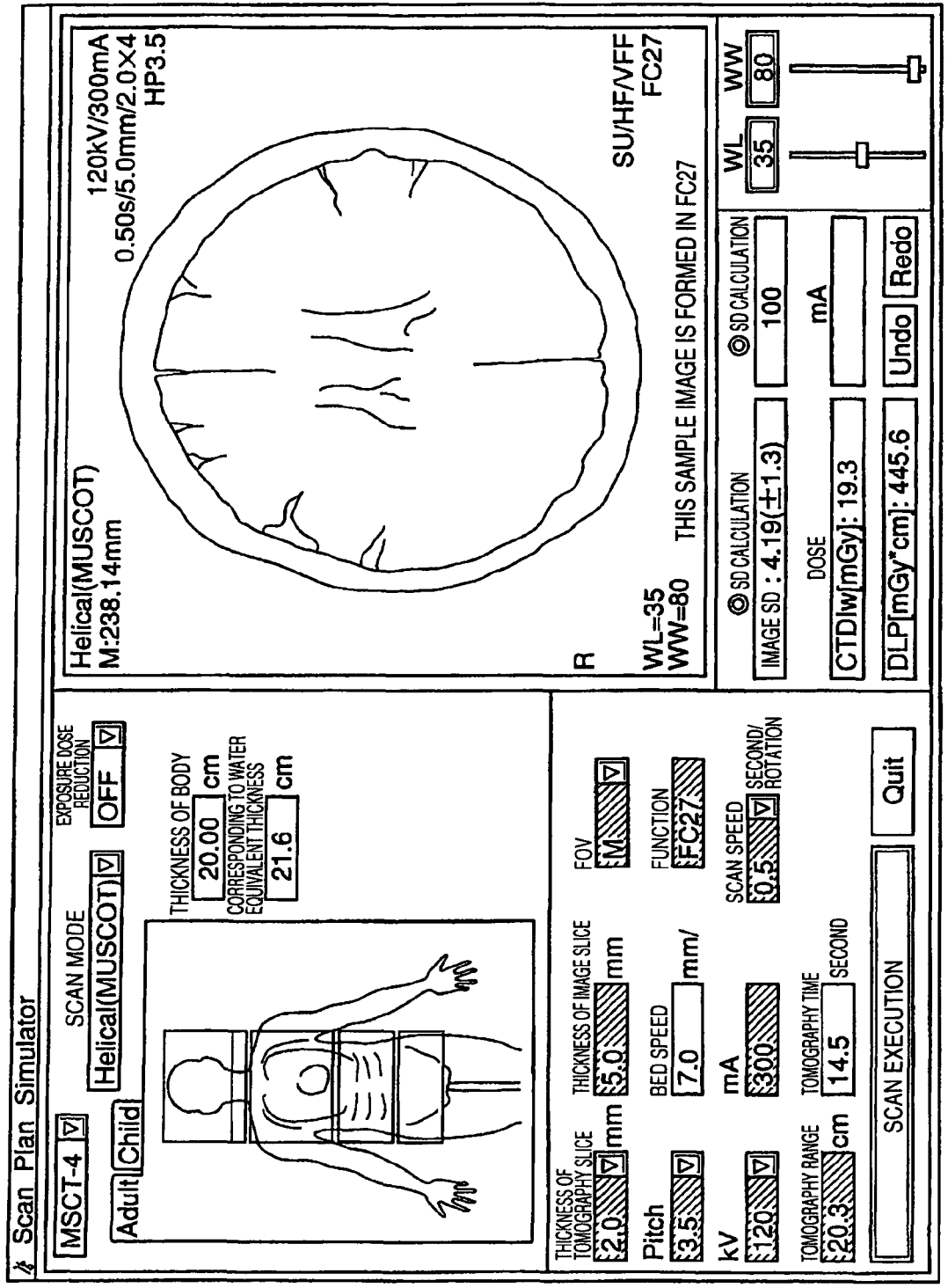
FIG. 45 is a diagram illustrating the result of a simulation distributed by clicking a [Protocol Simulator] button in detailed information of the examination protocol of FIG. 44.

When the button 338 of the 'Protocol Simulator' of the recommendation examination protocol of FIG. 44 is clicked, the data of the corresponding recommendation examination protocol is supplied to the exposure dose simulation unit 311. The exposure dose simulation unit 311 simulates the data collection (TOMOGRAPHY) and the image reconstruction according to the corresponding recommendation examination protocol. The simulation result is transmitted to the client side terminals 319 and 320 via the screen display unit 312 from the exposure dose simulation unit 311 and is displayed as shown in FIG. 45. The simulation is repeated while arbitrarily changing the X-ray tube voltage value, the X-ray tube current value, the TOMOGRAPHY time, the slice thickness, and the helical time through the client side terminals 319 and 320. As a result, it is possible to search the desired examination protocol while evaluating the image quality or the exposure dose.

According to the examination protocol distribution system of the present embodiment, as the useful examination protocol, the clients can receive the distribution of the examination protocols which are already used in their hospitals or some other hospitals and of which the exposure dose is low in the examination that the exposure dose is abnormally shown and the examination that the examination part or object is the same.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A radiation report system comprising:
a storage unit which stores a plurality of records including an expose dose, an examination protocol, an examination part, and patient information which includes a patient's age and a patient's weight with regard to a radiation examination using a plurality of radiation diagnosis apparatuses;
a grouping unit which classifies the plurality of records stored in the storage unit into a plurality of groups based on at least one of the examination protocol, the examination part, and the patient information;
a threshold value determining unit which determines a threshold value for each group based on the plurality of records stored in the storage unit;
an exception record detecting unit which detects in each group an exception record having an expose dose which exceeds the threshold value;
a report creating unit which creates an expose report for each group based on the plurality of records stored in the storage unit; and
a server unit which serves data of the exposure report to a client side terminal,
wherein the threshold value determining unit updates the threshold value for each group based on the plurality of records excluding the exception record, and the update of the threshold value and the detection of the exception record are repeated for a predetermined number of times or until a predetermined condition is satisfied.

2. The radiation report system according to claim 1, further comprising:
an exposure dose distribution creating unit which creates for each group an expose dose distribution indicating a number of the records with respect to the exposure dose.

3. The radiation report system according to claim 2, wherein the exposure dose distribution is included in the exposure report.

4. The radiation report system according to claim 1, wherein the record further includes an examination start time and an order number which discriminates each radiation examination.

5. The radiation report system according to claim 1,
wherein the classified records are listed in the exposure report, and
the exception record is displayed in a different manner from the other records.

6. The radiation report system according to claim 1,
wherein the threshold value determining unit updates the threshold value at a predetermined period.

7. The radiation report system according to claim 1,
wherein the threshold value determining unit determines the threshold value based on an exposure dose distribution using an exposure dose as a variable and using the number of the records with respect to the expose dose as a frequency.

8. The radiation report system according to claim 1,
wherein the radiation report system is connected to the plurality of radiation diagnosis apparatuses through a network, and
the grouping unit classifies the plurality of records stored in the storage unit into a plurality of groups based on at least one of the examination protocol, the examination part and the patient information, and types of the radiation diagnosis apparatuses.

9. The radiation report system according to claim 1,
wherein the exposure dose is at least one of CTDI and DLP.

10. The radiation report system according to claim 1,
wherein the examination protocol is at least one of a TOMOGRAPHY condition, an image generating condition, a display condition, a filming condition, and an archive condition or combination of them.

11. The radiation report system according to claim 1,
wherein the radiation diagnosis apparatus is a multi-slice CT apparatus, and
the examination protocol includes the number of scan slices, a thickness of the scan slice, a thickness of a reconstruction slice, and a kind of a reconstructing algorithm.

12. A radiation diagnosis apparatus comprising:
an examination unit which carries out a radiation examination with respect to an object to be examined;
a storage unit which stores a plurality of records including an exposure dose, an examination protocol, an examination part, a patient's age and a patient's weight with regard to the radiation examination;
a grouping unit which classifies the plurality of records stored in the storage unit into a plurality of groups based on at least one of the examination protocol, the examination part, and the patient information;
a threshold value determining unit which determines a threshold value for each group based on the plurality of records stored in the storage unit;
an exception record detecting unit which detects in each group an exception record having an expose dose which exceeds the threshold value;
a report creating unit which creates an exposure report for each group based on the plurality of records stored in the storage unit; and
a display unit which displays the exposure report,
wherein the threshold value determining unit updates the threshold value for each group based on the plurality of records excluding the exception record, and the update of the threshold value and the detection of the exception record are repeated for a predetermined number of times or until a predetermined condition is satisfied.

13. An examination protocol distribution system comprising:
a storage unit which stores a plurality of records including an exposure dose, an examination protocol and an examination object with regard to a plurality of radiation examinations carried out by a plurality of radiation diagnosis apparatuses arranged in a plurality of hospitals;
a threshold value determining unit which determines a threshold value based on the plurality of records stored in the storage unit;
an exception record detecting unit which detects, based on the threshold value, an exception record of which the exposure dose has an exception value from the plurality of records stored in the storage unit;
a searching unit which searches from the storage unit the data of a plurality of examination protocols in another hospital of which the examination object is the same as the exception record; and
a server unit which serves a client side terminal data of the exception record and the searched data of the examination protocol of another hospital;
wherein the storage unit stores data of a plurality of recommendation examination protocols;
the searching unit searches the examination protocols of another hospital and the recommendation examination protocols;
the server unit transmits to the client side terminal the searched recommendation examination protocols together with data of the exception record and data of the searched examination protocols of another hospital; and
the threshold value determining unit updates the threshold value based on the plurality of records excluding the exception record, and the update of the threshold value and the detection of the exception record are repeated for a predetermined number of times or until a predetermined condition is satisfied.

14. The examination protocol distribution system according to claim 13,
wherein the searching unit permutates the plurality of searched examination protocols according to the exposure dose.

15. The examination protocol distribution system according to claim 13, further comprising:
a report creating unit which creates for each hospital a report including a list of the examination protocols and the exposure doses.

16. The examination protocol distribution system according to claim 13,
wherein the data of the searched examination protocols of another hospital is served with the client side terminal together with sample image data corresponding to the searched examination protocols of another hospital.

17. The examination protocol distribution system according to claim 13, further comprising:
a simulation unit which performs an examination simulation according to the examination protocol designated through the client side terminal.

* * * * *